United States Patent
Misawa

(10) Patent No.: US 10,029,418 B2
(45) Date of Patent: Jul. 24, 2018

(54) LIVING BODY TISSUE THREE-DIMENSIONAL MODEL AND PRODUCTION METHOD THEREFOR

(71) Applicant: TERUMO CORPORATION, Shibuya-ku, Tokyo (JP)

(72) Inventor: Hiroshi Misawa, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 223 days.

(21) Appl. No.: 14/736,952

(22) Filed: Jun. 11, 2015

(65) Prior Publication Data
US 2015/0343710 A1 Dec. 3, 2015

Related U.S. Application Data

(60) Division of application No. 12/891,318, filed on Sep. 27, 2010, which is a continuation of application No. PCT/JP2009/056912, filed on Mar. 27, 2009.

(30) Foreign Application Priority Data

Mar. 28, 2008 (JP) ................................ 2008-086398
Mar. 28, 2008 (JP) ................................ 2008-086399

(Continued)

(51) Int. Cl.
*A61B 5/02* (2006.01)
*B29C 67/00* (2017.01)
(Continued)

(52) U.S. Cl.
CPC .......... *B29C 67/0088* (2013.01); *A61B 6/032* (2013.01); *A61B 6/504* (2013.01);
(Continued)

(58) Field of Classification Search
USPC ................................................ 264/401, 40.1
See application file for complete search history.

(56) References Cited

U.S. PATENT DOCUMENTS

| 6,017,973 A | 1/2000 | Tamura et al. |
| 2005/0186361 A1 | 8/2005 | Fukuda et al. |
| (Continued) | | |

FOREIGN PATENT DOCUMENTS

| EP | 1536395 A1 | 1/2015 |
| JP | 5-11689 A | 1/1993 |
| (Continued) | | |

OTHER PUBLICATIONS

International Search Report (PCT/ISA/210) dated Jun. 16, 2009, by Japanese Patent Office as the International Searching Authority for International Application No. PCT/JP2009/056912.

(Continued)

*Primary Examiner* — Christian Jang
*Assistant Examiner* — Mitchell E Alter
(74) *Attorney, Agent, or Firm* — Buchanan Ingersoll & Rooney PC

(57) ABSTRACT

An internal tissue including a lesion region in the human body is modeled as a three-dimensional model. By reconstructing thickness or flexibility of a lumen wall portion including the lesion region and making it possible to confirm a motion of the lumen wall or a flow of fluid in the inside of the lumen wall, a state of the lesion region in the lumen can be confirmed clearly by visual inspection or the like. As a result, the diagnosis in the lumen can be made easier.

7 Claims, 28 Drawing Sheets

(30) Foreign Application Priority Data

Mar. 28, 2008 (JP) ................................ 2008-086400
Mar. 28, 2008 (JP) ................................ 2008-086401

(51) Int. Cl.

| | |
|---|---|
| *A61B 6/03* | (2006.01) |
| *A61B 6/00* | (2006.01) |
| *G09B 23/30* | (2006.01) |
| *B29C 64/135* | (2017.01) |
| *B29C 64/386* | (2017.01) |
| *B29L 31/00* | (2006.01) |
| *A61B 17/00* | (2006.01) |
| *A61B 34/10* | (2016.01) |

(52) U.S. Cl.
CPC .......... *B29C 64/135* (2017.08); *B29C 64/386* (2017.08); *G09B 23/30* (2013.01); *A61B 2017/00716* (2013.01); *A61B 2034/105* (2016.02); *B29L 2031/753* (2013.01)

(56) References Cited

U.S. PATENT DOCUMENTS

| | | | |
|---|---|---|---|
| 2007/0116332 A1 | 5/2007 | Cai et al. | |
| 2008/0033569 A1* | 2/2008 | Ferren | A61B 1/00156 623/23.7 |
| 2008/0187895 A1* | 8/2008 | Sakezles | G09B 23/306 434/268 |

FOREIGN PATENT DOCUMENTS

| | | | |
|---|---|---|---|
| JP | 5-50477 A | 7/1993 | |
| JP | 5-50477 U | 7/1993 | |
| JP | 8-1874 A | 1/1996 | |
| JP | 9-169827 A | 6/1997 | |
| JP | 2004-275682 A | 10/2004 | |
| JP | 3613568 B2 | 1/2005 | |
| JP | 2005-40299 A | 2/2005 | |
| JP | 2005-040299 A | 2/2005 | |
| JP | 2006-2087 A | 1/2006 | |
| JP | 2006-343434 A | 12/2006 | |
| JP | 2007-185242 A | 7/2007 | |
| WO | 2006/083963 A2 | 8/2006 | |

OTHER PUBLICATIONS

Chinese First Office Action (English transaltion) issued in corresponding Chinese Patent Application No. 200980110436.3 (5 pages), CN Office Action previously cited in an Information Disclosure Statement on Nov. 19, 2013.
Chinese Second Office Action (English translation) issued in corresponding Chinese Patent Application No. 200980110436.3 (7 pages). CN Office Action previously cited in an Information Disclosure Statement on Nov. 19, 2013.
Chinese Third Office Action (English translation) issued in corresponding Chinese Patent Application No. 200980110436.3 (8 pages). CN Office Action previously cited in an Information Disclosure Statement on Nov. 19, 2013.
Chinese Fourth Office Action (English translation) issued in corresponding Chinese Patent Application No. 200980110436.3 (4 pages).
Notification of Reasons for Refusal (English translation) dated May 31, 2017, by the Japanese Patent Office in corresponding Japanese Patent Application No. 2010-505986 (4 pages).
European Communication and Search Report dated May 15, 2015 issued in the corresponding European Patent Application No. 09726020.2-1956.

* cited by examiner

FIG.4(A) FRONT VERTICAL SECTIONAL DATA D21
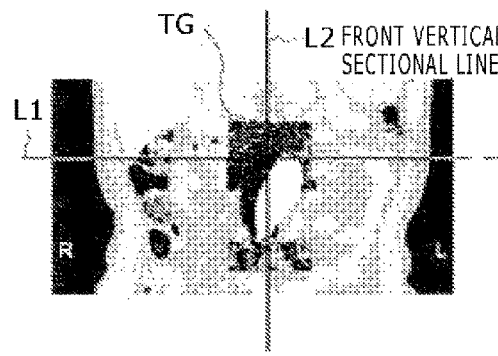
FIG.4(B) SIDE VERTICAL SECTIONAL DATA D31
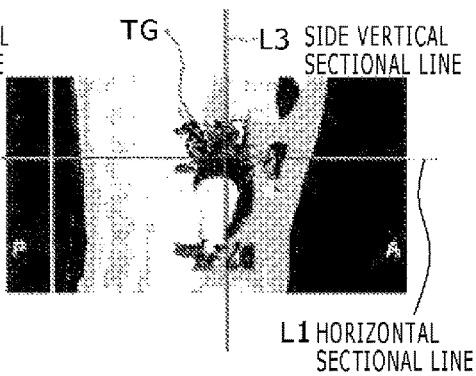
FIG.4(C) HORIZONTAL SECTIONAL DATA D11
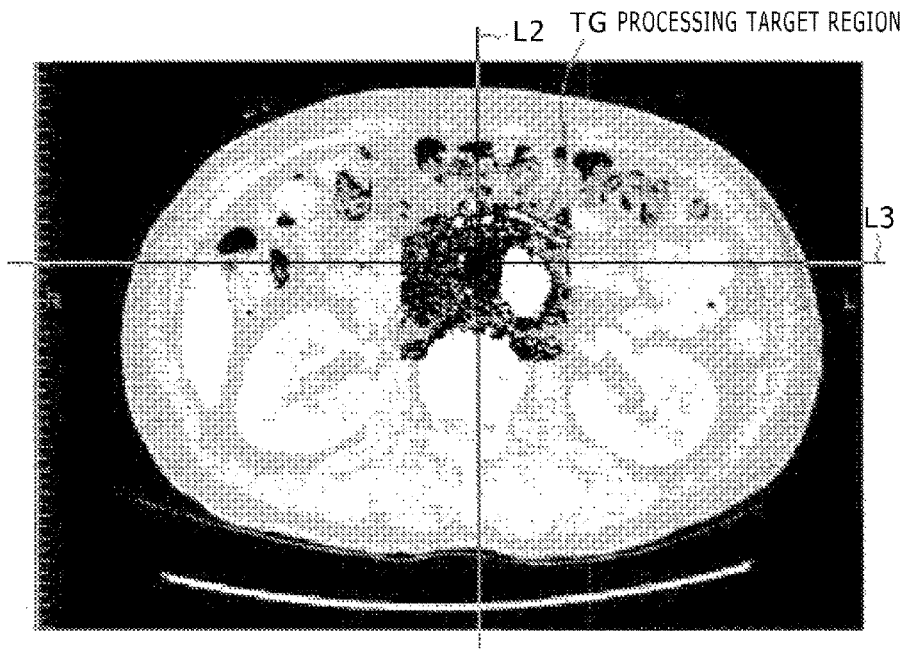

FIG. 5(A) FRONT VERTICAL SECTIONAL DATA D21
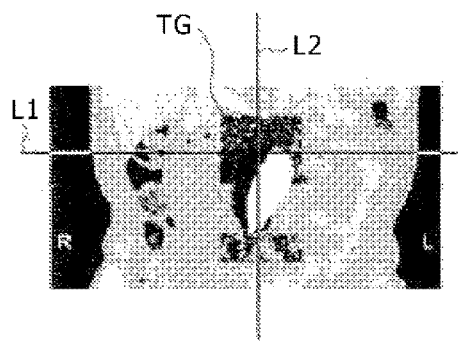
FIG. 5(B) SIDE VERTICAL SECTIONAL DATA D31
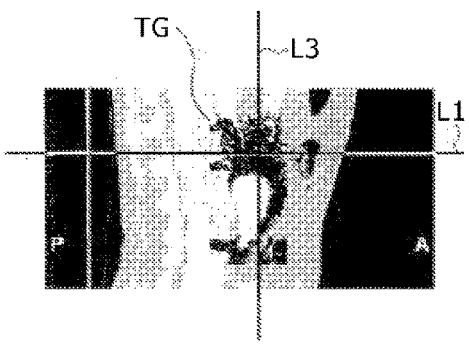
FIG. 5(C) HORIZONTAL SECTIONAL DATA D11
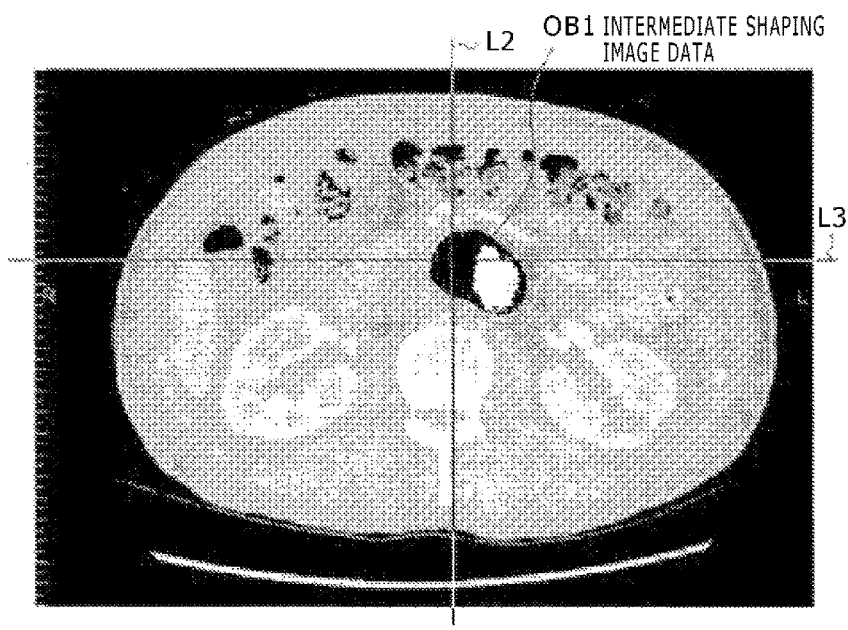

FIG. 6(A) FRONT VERTICAL SECTIONAL DATA D22
FIG. 6(B) SIDE VERTICAL SECTIONAL DATA D32
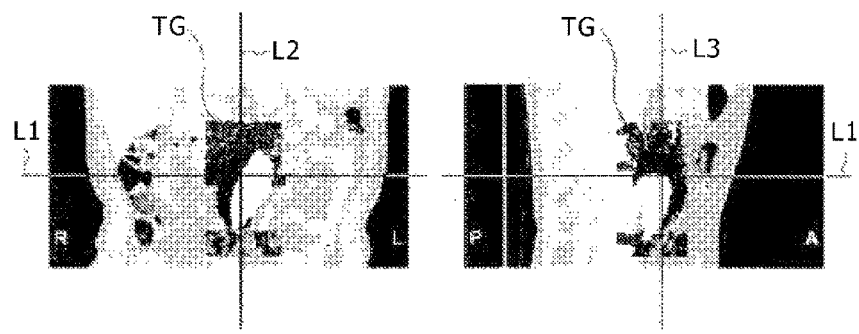
FIG. 6(C) HORIZONTAL SECTIONAL DATA D12
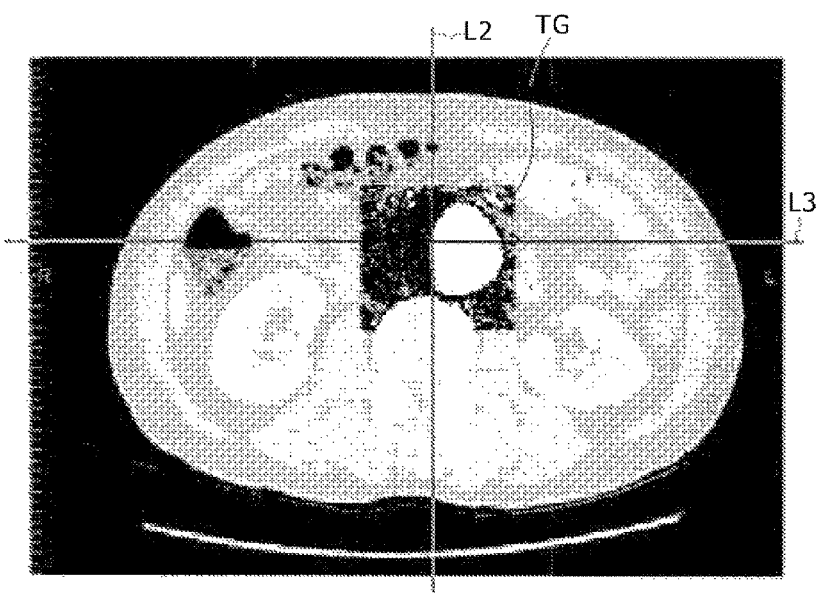

FIG. 7(A) FRONT VERTICAL SECTIONAL DATA D22   FIG. 7(B) SIDE VERTICAL SECTIONAL DATA D32
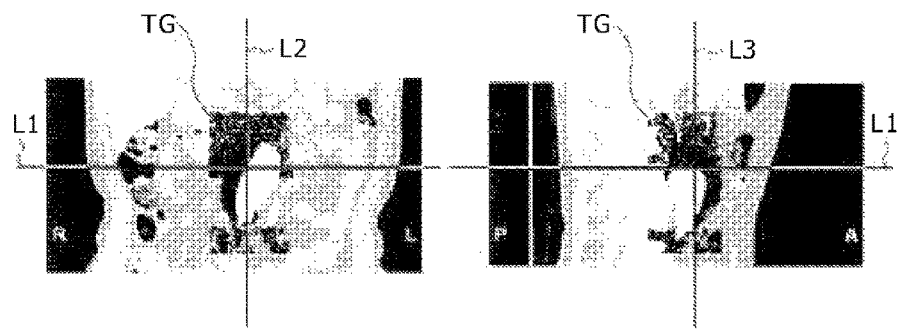
FIG. 7(C) HORIZONTAL SECTIONAL DATA D12
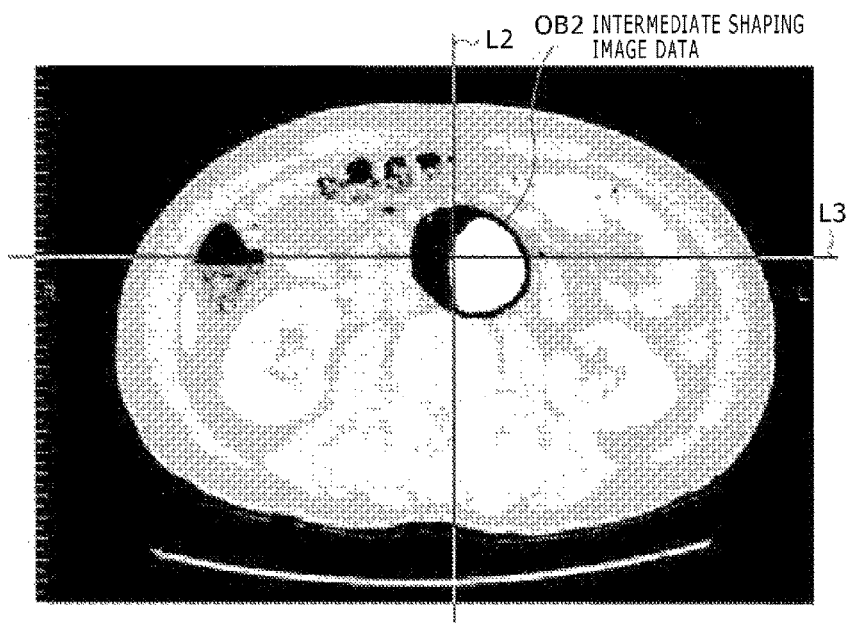

FIG. 8(A) FRONT VERTICAL SECTIONAL DATA D23
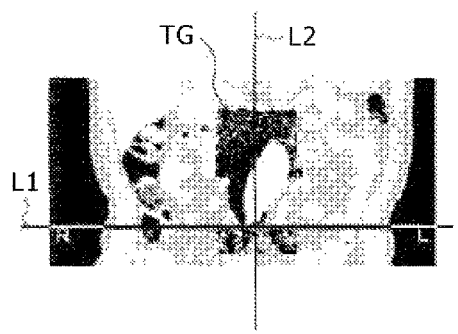
FIG. 8(B) SIDE VERTICAL SECTIONAL DATA D33
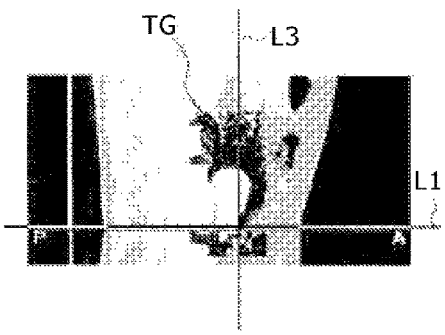
FIG. 8(C) HORIZONTAL SECTIONAL DATA D13
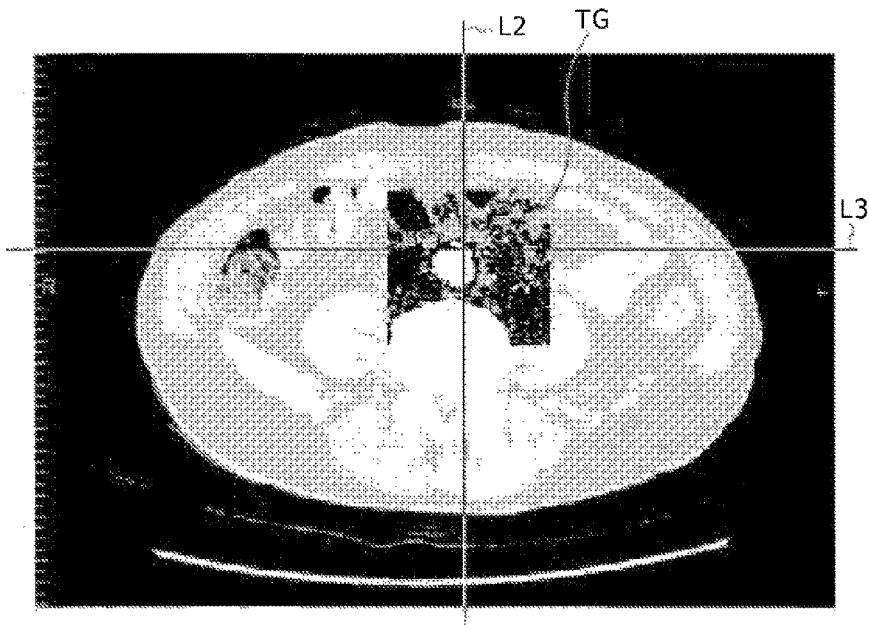

FIG. 9(A) FRONT VERTICAL SECTIONAL DATA D23  FIG. 9(B) SIDE VERTICAL SECTIONAL DATA D33
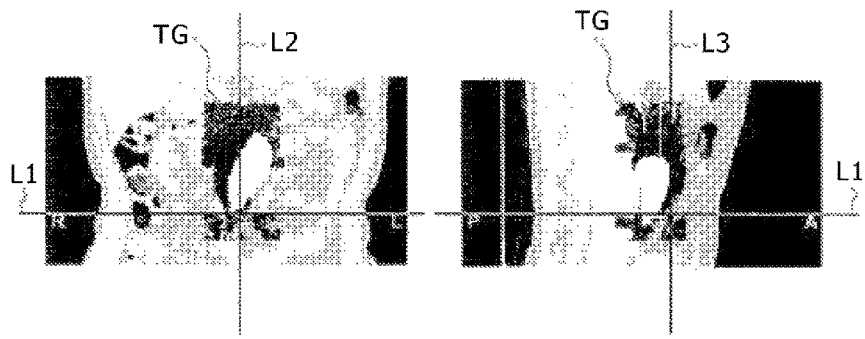
FIG. 9(C) HORIZONTAL SECTIONAL DATA D13
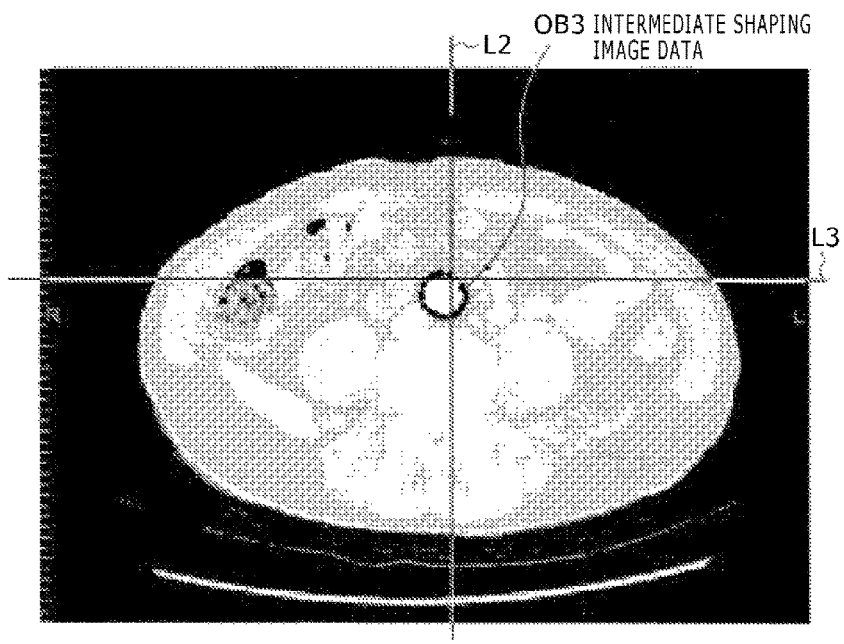

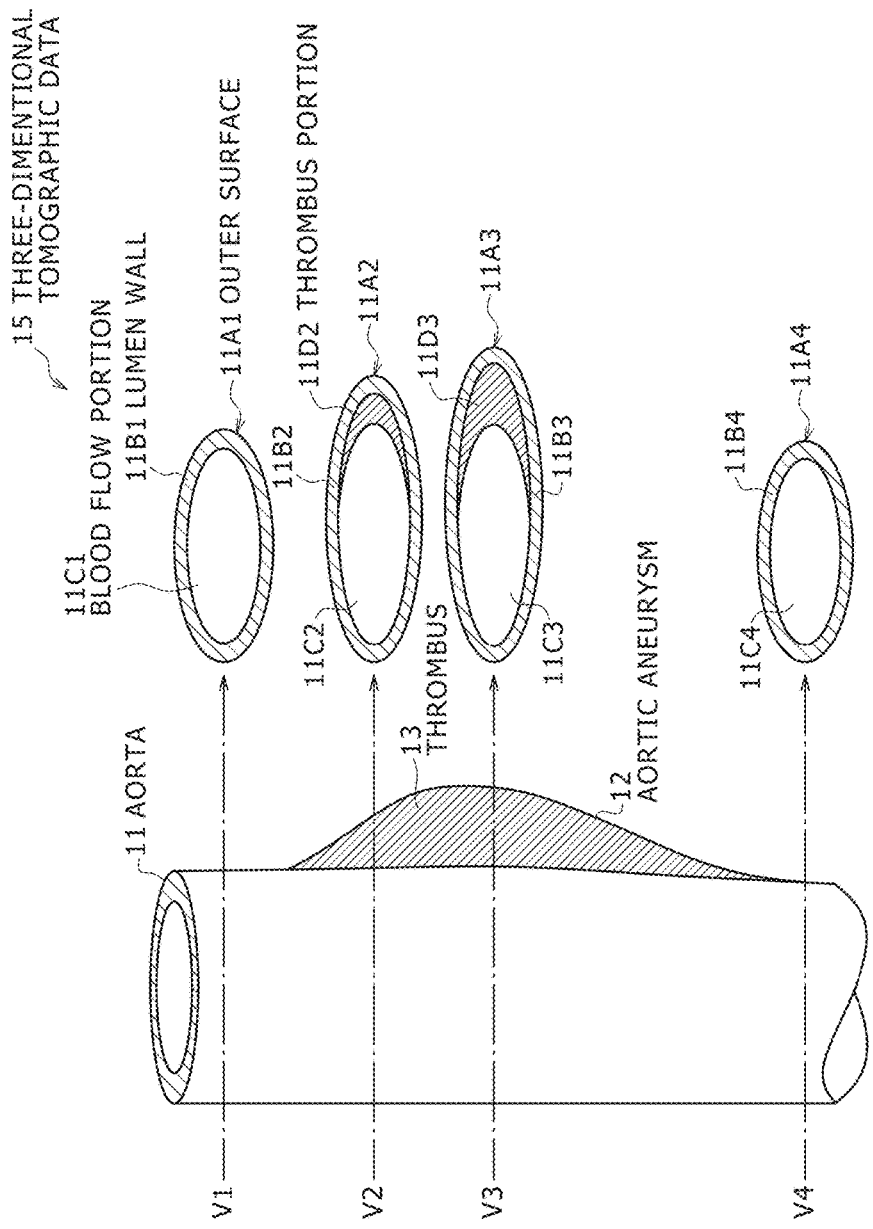

FIG.23
(A)
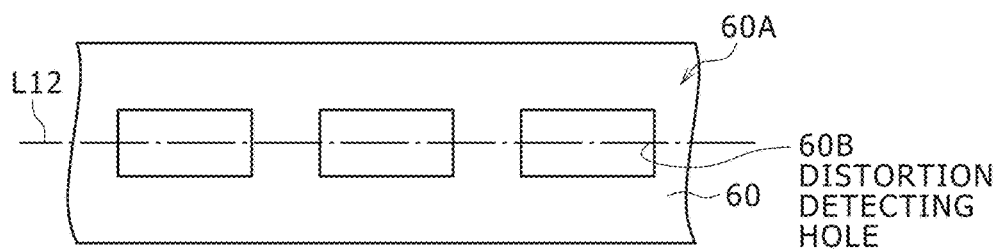
(B)
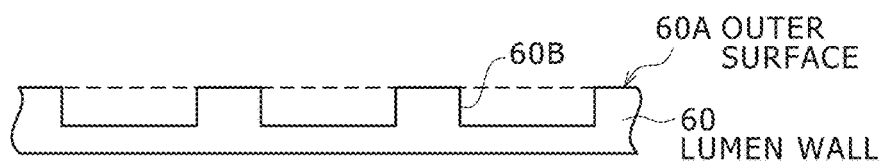
(C)
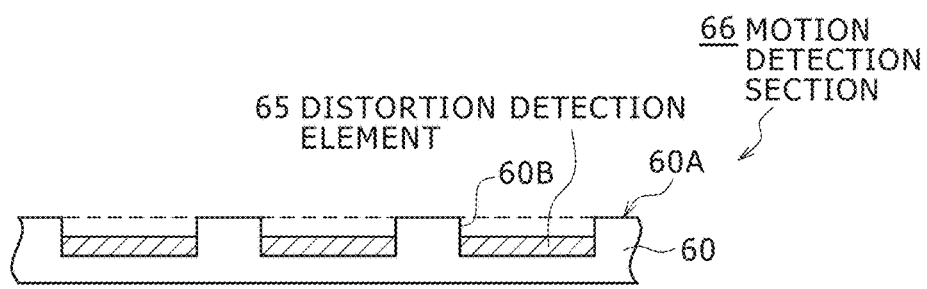

FIG.25
(A)
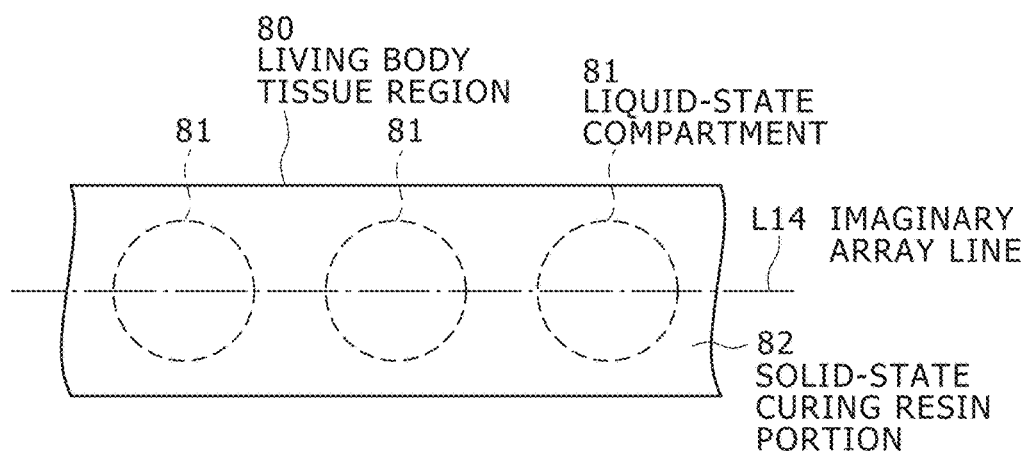
(B)
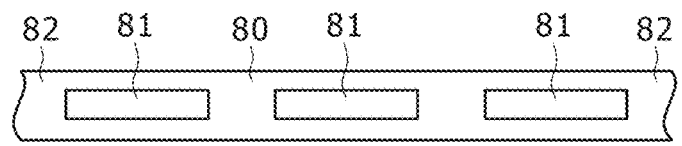

FIG.28

1······LIVING BODY TISSUE THREE-DIMENSIONAL MODEL PRODUCTION SYSTEM, 2······THREE-DIMENSIONAL DATA ACQUISITION APPARATUS, 3······IMAGE DATA PROCESSING APPARATUS, 4······THREE-DIMENSIONAL MODEL PRODUCTION APPARATUS, 5······THREE-DIMENSIONAL MODEL, 11······AORTA, 11A~11A4······OUTER SURFACE, 11B1~11B4······LUMEN WALL, 11C1~11C4······BLOOD FLOW PORTION, 11D2,11D3······THROMBUS PORTION, 12······AORTIC ANEURYSM, 13······THROMBUS, 21······AORTA, 21A1~21A5······BOUNDARY, 21B2~21B5······DOUBLE BLOOD VESSEL WALL, 21C1~21C5······LUMEN WALL, 22······SWELLING, 23······DOUBLE BLOOD VESSEL WALL, 31······AORTIC ARCH OF PECTORAL REGION, 31A1~31A6······BOUNDARY, 31B1~31B6······BLOOD FLOW, 31C1~31C6······LUMEN WALL, 32······BRACHIOCEPHALIC ARTERY, 33······LEFT COMMON CAROTID ARTERY, 34······LEFT SUBCLAVIAN ARTERY, 41······HEART, 42······AORTA, 44······BYPASS BLOOD VESSEL, 45A~45D······BOUNDARY, 46A~46C······BLOOD FLOW, 47, 48······CONNECTING BLOOD VESSEL PORTION, 49······BYPASS BLOOD VESSEL PORTION, 50B~50D······BLOOD FLOW, 51······FLOW INDICATING ELEMENT, 51A······LEG PORTION, 51B······FLOW ABUTTING PORTION, 52······LUMEN WALL, 53······LUMEN INNER FACE, 54······LUMEN, 60······LUMEN WALL, 60A······OUTER SURFACE, 60B······DISTORTION DETECTING HOLE, 60C······FLEXIBLE PORTION, 60D······HARDENED PORTION, 60E······UNHARDENED PORTION, 60F,60G······HARDENED PLATE PORTION, 61······MOTION DETECTING PROTRUSION, 62,66,69······MOTION DETECTION SECTION, 70······PRESSURE SENSING MECHANISM, 71······DISPLACEMENT DETECTION SECTION, 71A······LIGHT EMITTING ELEMENT, 71B······LIGHT RECEIVING ELEMENT, 72······DISPLACEMENT DETECTION SECTION, 72A······DETECTOR BODY, 72B······PRESSURE SENSING PLATE, 72C······CONTACT ELEMENT, 80······LIVING BODY TISSUE REGION, 81······LIQUID-STATE COMPARTMENT, 82······SOLID-STATE CURING RESIN PORTION, 83······LUMEN WALL

LIVING BODY TISSUE THREE-DIMENSIONAL MODEL AND PRODUCTION METHOD THEREFOR

This application is a Divisional of U.S. application Ser. No. 12/891,318 filed on Sep. 27, 2010, which is a Continuation of International Application No. PCT/JP2009/056912 filed on Mar. 27, 2009, and claims priority to Japanese Application No. 2008-086398 filed on Mar. 28, 2008, Japanese Application No. 2008-086399 filed on Mar. 28, 2008, Japanese Application No. 2008-086400 filed on Mar. 28, 2008 and Japanese Application No. 2008-086401 filed on Mar. 28, 2008, the entire content of all of which are incorporated herein by reference

TECHNICAL FIELD

The present invention generally pertains to a living body tissue three-dimensional model and method for producing such a three-dimensional model. More specifically, the invention here relates to a living body tissue three-dimensional model and method for producing such a three-dimensional model having particularly useful application to reconstruct living body tissue having a lesion region inside a human body.

BACKGROUND DISCUSSION

A three-dimensional model for reconstructing a living body tissue inside a human body has been proposed in which tomographic image information is obtained utilizing data of X-ray CT or data of MRI using a contrast medium and then a living body tissue is reconstructed based on three-dimensional data obtained from the tomographic image information. The following patent documents, identified as Patent Documents 1 to 4, disclose examples.
Patent Document 1—Japanese Patent Laid-Open No. Hei 8-1874
Patent Document 2—Japanese Patent Laid-Open No. 2006-343434
Patent Document 3—Japanese Patent Laid-Open No. Hei 5-11689
Patent Document 4—Japanese Patent No. 3613568

When the presence of a lesion region appearing in a living body tissue of the living body, particularly a lesion region inside the human body, is confirmed and treatment of the lesion region is investigated, it is impossible for a doctor to diagnose the lesion region while directly visually inspecting the lesion region. Therefore, if a living body tissue three-dimensional model of a lesion region inside a human body can be reconstructed and presented, this has high effectiveness as a tool for carrying out suitable treatment.

With respect to a living body tissue having a bore or lumen such as a blood vessel, diagnosis and treatment of a lesion region also can be carried out by passing an operation instrument such as a catheter into the bore or lumen. There would thus be a relatively high practical use for being able to reconstruct a three-dimensional model of a living body tissue in which a lesion region appears.

Regarding a living body tissue having a tube-like lumen such as a blood vessel, if the manner of fluid flow such as blood flow in a lumen can be found utilizing a three-dimensional model, this would be effective to confirm a function of a living body tissue.

Living body tissue having a tube-like lumen such as a blood vessel, where the pressure of fluid, for example, blood, which passes in a lumen varies, a living body tissue expands and contracts. If the pressure in the lumen becomes excessively high as a result of insertion of a manipulation instrument into a lumen or expansion or the like of a manipulation instrument in a lumen, it is possible that a lesion region of the living body tissue may experience or undergo an improper movement causing, for example, a rupture.

In this regard, identifying movement of a living body tissue reconstructed by a reconstruction structure model is not provided in the past, and the existing techniques are thus still insufficient as a living body tissue model. Where, for example, a method of hardening light-curing resin using light generated from three-dimensional data is used as a method of reconstructing a living body tissue based on three-dimensional data in the past, since the living body tissue three-dimensional model is reconstructed by hardening active energy-curing resin, it has rigidity higher than that of a living body tissue and therefore is lacking in flexibility. Therefore, the living body tissue three-dimensional model does not reconstruct the flexibility of living body tissue, and enhancement of a function as an operation maneuver simulator such as to confirm compatibility with a stent or stent graft is desirable or demanded.

SUMMARY

The disclosure here contemplates a living body tissue three-dimensional model and production method which make it possible to appropriately reconstruct a lumen portion including a lesion region, make it possible to confirm fluid flow in a lumen in a living body tissue which has the lumen, by visual inspection, or make it possible to grasp, when pressure in a lumen varies, a variation of a region of a living body tissue which occurs in response to the variation of the pressure or else make it possible to produce a living body tissue three-dimensional model so as to have flexibility using hardened resin of active energy-curing resin.

According to one aspect, a living body tissue three-dimensional model includes a three-dimensional model of a lumen wall portion of a lumen portion of an actual living body so the three-dimensional model is a three-dimensional model of the lumen portion of the actual living body. The three-dimensional model is configured to possess or reconstruct the thickness of the lumen wall portion of the lumen portion including a reconstructed lesion region of the actual living body The living body tissue three-dimensional model may be configured such that a living body lumen model produced based on tomographic image data of a living body has a projecting plate (thin plate) extending from a lumen wall toward a lumen.

The living body tissue three-dimensional model can also be configured such that pressure in a lumen surrounded by a lumen wall in a living body model produced based on tomographic image data of a living body is measured through displacement in response to a variation of the pressure in the lumen. The measurement can occur with a measuring structure provided on the lumen wall.

The living body tissue three-dimensional model can additionally be configured such that a living body model produced by hardening liquid-state active energy-curing resin based on tomographic image data of a living body has a liquid-state compartment in which the active energy-curing resin remains unhardened and is surrounded by the hardened resin.

With the three-dimensional model and method disclosed here, the thickness of the lumen wall portion including the lesion region of the actual living body is reconstructed and so the state of the lesion region in the lumen can be visually inspected clearly. As a result, the diagnosis in the lumen can be carried out more easily. Also, the plate projecting from the lumen wall toward the lumen allows the flowing manner of fluid which flows in the lumen to be confirmed by visually inspecting movement of the plate which moves so as to correspond to the flowing manner of the fluid.

The lumen wall surrounding the lumen is produced based on tomographic image data of a living body, and the measuring structure is formed on the lumen wall such that pressure in the lumen is measured through displacement which occurs with the measuring structure. This thus allows motion which occurs with the lumen wall by a variation of the pressure in the lumen to be measured with relative certainty.

Because the living body model of the actual living body tissue is produced by carrying out a hardening process of active energy-curing resin, it is possible to provide the unhardened liquid-state compartment enclosed in the hardened resin, and so a living body image main model of a soft touch can be obtained.

BRIEF DESCRIPTION OF THE DRAWING FIGURES

FIG. 4A is a cross-sectional view showing front vertical sectional data D21, FIG. 4B is a cross-sectional view showing side vertical sectional data D31, and FIG. 4C is a cross-sectional view showing horizontal sectional data D11, regarding upper stage tomographic data.

FIG. 5A is a cross-sectional view showing intermediate shaping image data of the upper stage tomographic data in FIG. 4A, FIG. 5B is a cross-sectional view showing intermediate shaping image data of the upper stage tomographic data in FIG. 4B, and FIG. 5C is a cross-sectional view showing intermediate shaping image data of the upper stage tomographic data in FIG. 4C.

FIG. 6A is a cross-sectional view showing front vertical sectional data, FIG. 6B is a cross-sectional view showing side vertical sectional data, and FIG. 6C is a cross-sectional view showing middle stage tomographic data, of middle stage tomographic data.

FIG. 7A is a cross-sectional view showing intermediate shaping image data of the middle stage tomographic data in FIG. 6A, FIG. 7B is a cross-sectional view showing intermediate shaping image data of the middle stage tomographic data in FIG. 6B, and FIG. 7C is a cross-sectional view showing intermediate shaping image data of the middle stage tomographic data in FIG. 6C.

FIG. 8A is a cross-sectional view showing front vertical sectional data, FIG. 8B is a cross-sectional view showing side vertical section data, and FIG. 8C is a cross-sectional view showing horizontal sectional data, of lower stage tomographic data.

FIG. 9A is a cross-sectional view showing intermediate shaping image data of the lower stage tomographic data in FIG. 8A, FIG. 9B is a cross-sectional view showing intermediate shaping image data of the lower stage tomographic data in FIG. 8B, and FIG. 9C is a cross-sectional view showing intermediate shaping image data of the lower stage tomographic data in FIG. 8C.

FIG. 10 is a schematic view illustrating a process where a thrombus exists in an aortic aneurysm.

FIG. 23 is schematic views illustrating motion detection operation by a distortion detection element.

FIG. 25 is schematic views illustrating a formation process of a liquid-state compartment.

Figure 1:
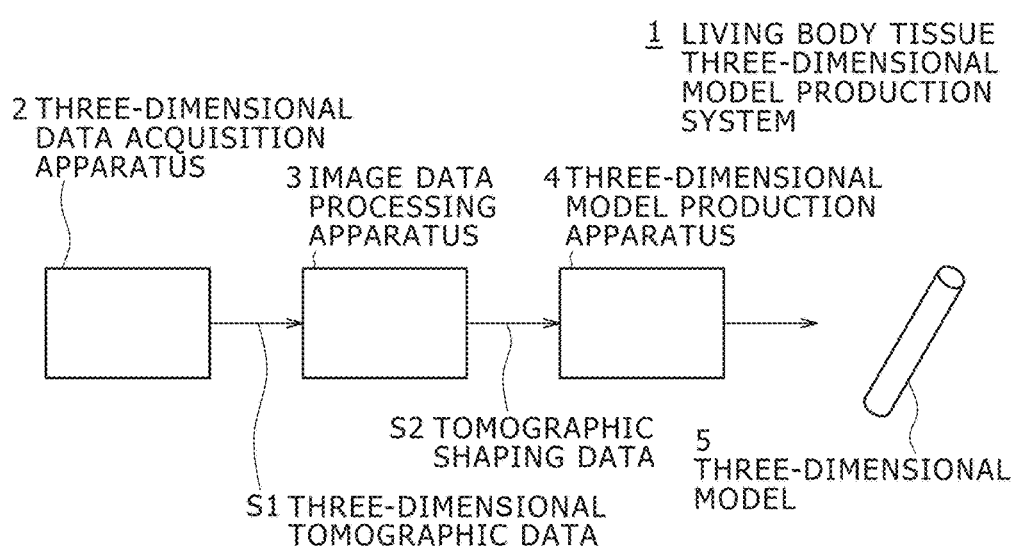
FIG. 1 is a block diagram of a living body tissue three-dimensional model production system according to an embodiment disclosed here.

DETAILED DESCRIPTION (1) Living Body Tissue Three-Dimensional Model Production System FIG. 1 illustrates a living body tissue three-dimensional model production system 1. The living body tissue three-dimensional model production system includes a three-dimensional data acquisition apparatus 2 which acquires from a subject a three-dimensional tomographic data S1 of a region including a living body tissue whose living body tissue three-dimensional model is to be produced. The acquired data is transferred to an image data processing apparatus 3 of the living body tissue three-dimensional model production system.

In this embodiment, the three-dimensional data acquisition apparatus 2 is in the form of an X-ray CT apparatus, and acquires the three-dimensional tomographic data S1 including 100 to 300 tomographic images (300 tomographic images in this example), obtained by slicing, with a slice width of 1 mm, a lesion region of an aorta which is a living body tissue, and then supplies the three-dimensional tomographic data S1 to the image data processing apparatus 3.

The image data processing apparatus 3 extracts image data of a living body tissue region (in the case of the embodiment, a lesion region of an aorta) to be shaped as a living body tissue three-dimensional model from the image data for each slice of the three-dimensional tomographic data S1 and carries out an interpolation editing process for the extracted image data as the occasion demands.

Thus, the image data processing apparatus 3 produces and supplies tomographic shaping data S2 including planar point data of multi layers to a three-dimensional model production apparatus 4 of the living body tissue three-dimensional model production system.

In this embodiment, the three-dimensional model production apparatus 4 is comprised of an optical shaping apparatus, and irradiates ultraviolet laser light on a liquid surface of liquid-state light-curing resin at a position of the point data for each slice of the tomographic shaping data S2 to harden the resin slices in a predetermined thickness for each slice and laminates the hardened light-curing resin for each slice of the tomographic shaping data S2 to form a three-dimensional model 5 wherein the hardened slices are connected three-dimensionally.

Here, as the three-dimensional model production apparatus 4, for example, an optical shaping apparatus of a lamination pitch 0.05 [mm], CMET Inc., RM-3000, can be applied.

This optical shaping apparatus repetitively carries out lamination operation for selectively irradiating ultraviolet laser light controlled by a computer so that a desired pattern is obtained on a liquid surface of liquid-state light-curing resin placed in a container to harden the fluid light-curing resin in a predetermined thickness and supplying liquid-state resin per one slice onto the hardened slice and then irradiating ultraviolet laser light to harden the liquid-state resin similarly as described above so that a continued hardened slice is obtained.

As the light-curing resin, a urethane acrylate-based light-curing resin composition such as disclosed in Japanese Patent Laid-Open No. Hei 9-169827 can be employed, and a silicon-based light-curing resin composition such as disclosed in Japanese Patent Laid-Open No. 2006-2087 can be applied.

Where a model of a living body tissue other than a bone and a tooth is to be produced, the above-described resin composition whose ductility is relatively high while having a relatively low Young's modulus is low or like resin composition is preferable.

(2) Image Data Processing Apparatus

Figure 2:
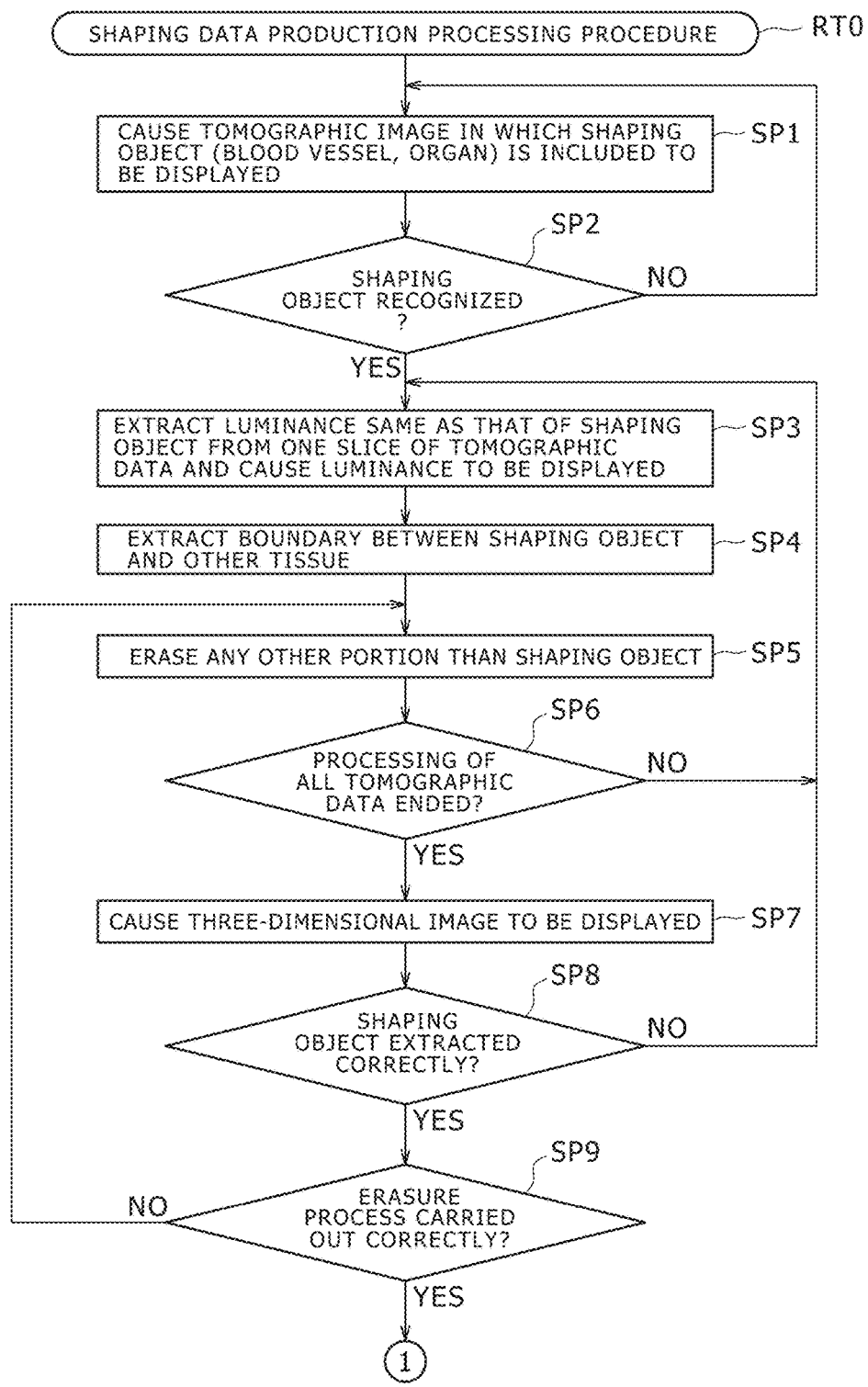
FIG. 2 is a flow chart illustrating a portion of the shaping data production processing procedure performed by the image data processing apparatus in FIG. 1.
Figure 3:
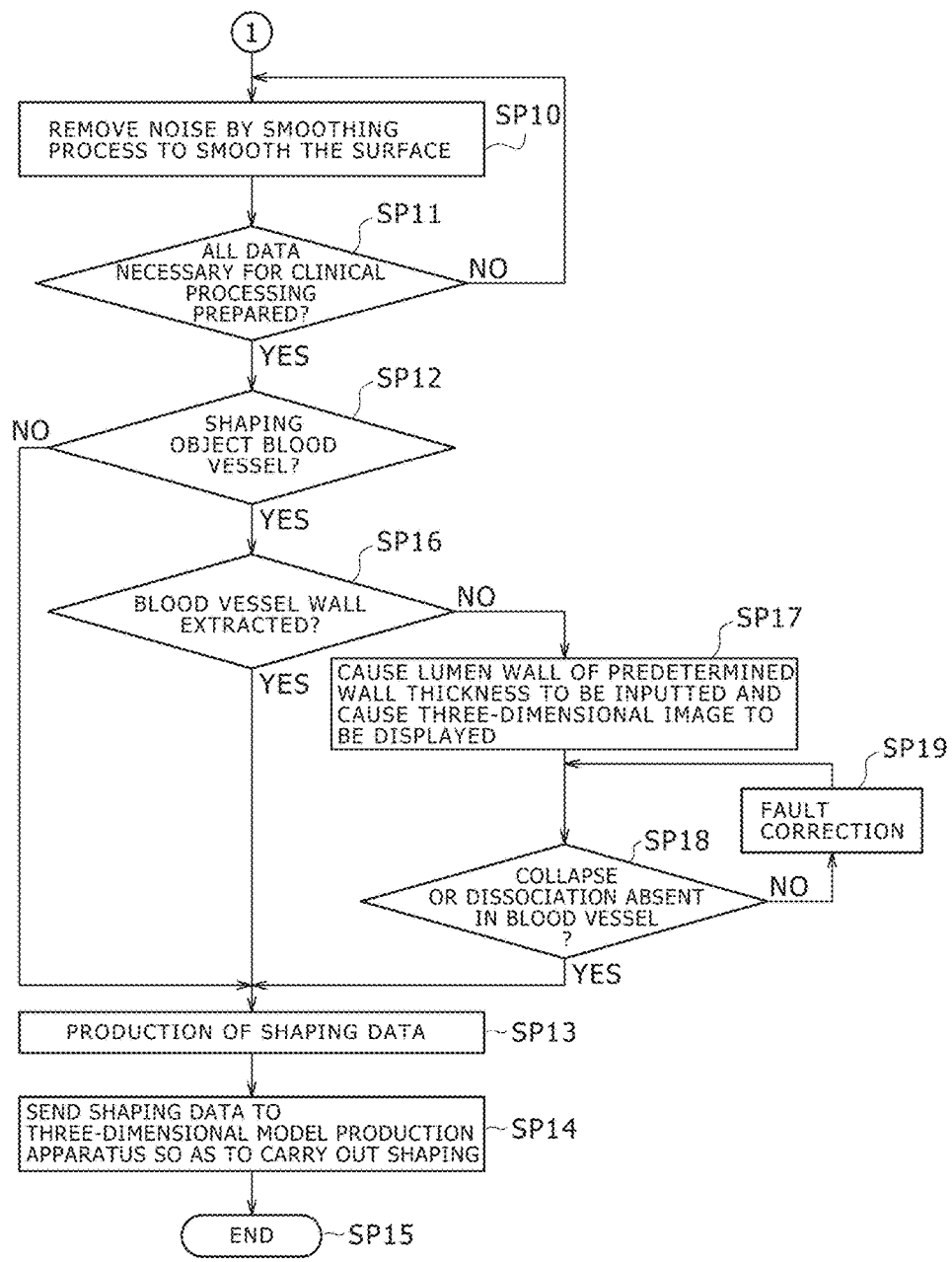
FIG. 3 is a flow chart illustrating a portion of the shaping data production processing procedure performed by the image data processing apparatus in FIG. 1.

The image data processing apparatus 3 carries out an image process for the three-dimensional tomographic data S1 supplied from the three-dimensional data acquisition apparatus 2 in accordance with a shaping data production processing procedure RT0 illustrated in FIGS. 2 and 3.

In the case of the present embodiment, the three-dimensional tomographic data S1 include, as shown as a representative example by tomographic data at an upper stage portion, a middle stage portion and a lower stage portion in FIGS. 4, 6 and 8, horizontal sectional data D11, D12 and D13, front vertical sectional data D21, D22 and D23 and side vertical sectional data D31, D32, and D33, by which a living body tissue of an image point at a three-dimensional position inside the body is represented by the brightness of luminance (accordingly, by the density of an image).

Here, the horizontal sectional data D11, D12 and D13 shown in FIG. 4(C), FIG. 6(C) and FIG. 8(C) represent tomographic data at a height of a horizontal sectional line L1 shown in the front vertical sectional data D21, D22 and D23 and the side vertical sectional data D31, D32 and D33 in FIG. 4(A), FIG. 6(A) and FIG. 8(A), and FIG. 4(B), FIG. 6(B) and FIG. 8(B), respectively.

Similarly, the front vertical sectional data D21, D22 and D23 and the side vertical sectional data D31, D32 and D33 in FIG. 4(A), FIG. 6(A) and FIG. 8(A), and FIG. 4(B), FIG. 6(B) and FIG. 8(B) represent vertical sectional data obtained at a position in a leftward and rightward direction of the human body and a position in a forward and rearward direction of the human body in accordance with a side vertical sectional line L3 and a front vertical sectional line L2 as shown in FIG. 4(C), FIG. 6(C) and FIG. 8(C), respectively.

Thus, by performing an appropriate operation designating the position of the horizontal sectional line L1, front vertical sectional line L2 and side vertical sectional line L3, the user of the image data processing apparatus 3 can select tomographic image data including a region of a living body tissue to be obtained as the tomographic shaping data S2 from within the tomographic data supplied as the three-dimensional tomographic data S1 to cause a display unit of the image data processing apparatus 3 to display the selected data, and can carry out editing operation (image process such as deletion, addition, changing or the like of image data regarding the region of the living body tissue in the image region designated as a target) for the displayed image data.

The image data processing apparatus 3 starts the shaping data production processing procedure RT0 shown in FIG. 2 and selects, first at step SP1, a tomographic image including a living body tissue such as a blood vessel, an organ or the like which is a shaping target (that is, a target) whose living body tissue three-dimensional model is to be formed in response to the designation operation by the user from within the three-dimensional tomographic data S1 and then causes the display unit to display the selected image on the display unit. Thereafter, at step SP2, the image data processing apparatus 3 causes the user to confirm whether or not the shaping target is correctly identified.

In the case of the present embodiment, the user would move the horizontal sectional line L1, front vertical sectional line L2 and side vertical sectional line L3 to search for a range of the tomographic image including the shaping target (for example, an aorta) inside the human body to identify a processing target region TG.

At this time, the image data processing apparatus 3 advances the processing to step SP3 in response to the designation operation by the user, and extracts those image data having a luminance the same as that of the shaping target from the three-dimensional tomographic data in the processing target region TG including the shaping target (that is, the target) and then causes the extracted data to be displayed on the display unit.

In the case of the present embodiment, taking a lesion region of an aorta as the target, the processing target region TG is set in regard to a heightwise range in the upward and downward direction including the target, a widthwise range in the leftward and rightward direction and a depthwise range in the forward and rearward direction, and one slice of the tomographic data which includes the processing target region TG, for example, the upper stage tomographic data shown in FIG. 4, is displayed on the display unit.

Here, the aorta designated as the target is a tube-formed living body tissue having a bore in which blood is filled, and, when the three-dimensional tomographic data S1 is acquired for a check of the lesion region by the three-dimensional data acquisition apparatus 2, image pickup is carried out using contrast medium. Therefore, the three-dimensional tomographic data S1 are fetched as such image data that the bore of the blood vessel has relatively light luminance by the image data processing apparatus 3.

On the other hand, in the horizontal sectional data D11 illustrated in FIG. 4(C), a lumen wall portion of the blood vessel in the processing target region TG is displayed as image data in which the lumen wall portion and the other tissue on the outer side (outwardly) of the lumen wall portion are not clearly distinguished from each other.

Therefore, at the next step SP4, the image data processing apparatus 3 extracts a boundary between the lumen wall portion of the blood vessel and the tissue on the outer side of the shaping target in accordance with the operation by the user.

The extraction operation is carried out while the position or the shape of the shaping object (that is, the aorta) inside the body of a healthy person is being assumed or information based on examples of dissection of patients having the same affection is being taken into consideration based on anatomical information.

In fact, when some difference exists in density between a blood vessel which is an object of extraction and the other organ, it is decided that an image data portion of a density the same as that of a lumen wall portion of a blood vessel is a blood vessel and is cut away from an image of the external tissue to carry out an extraction operation of the blood vessel along an outer wall of the shaping object.

Further, where it is impossible to cut away the blood vessel from the external tissue only with the horizontal sectional data D11 of FIG. 4 (C), horizontal sectional data above and below the horizontal sectional data D11 are referred to so that image data which conform to a flow of a plurality of tomographic images (flow from an upper position to a lower position or flow from a lower position to an upper position) are determined as image data of the shaping object and are cut away from the external tissue.

Further, once in a while, where the shaping object includes a lesion region, although there is no difference in density, an outer shape of the shaping object including the lesion region is different from that of an organ of an anatomically healthy person. The outer shape of the lesion region is for example, extraordinary swollen or extraordinary thin. Therefore, extraction of a boundary between the object image and the other organ including the difference is carried out.

When the extraction process of a boundary between the shaping object and the other tissue ends, the image data processing apparatus 3 carries out, at the next step SP5, a process of erasing the portion other than the shaping object from the processing target region TG.

As a result, the image data processing apparatus 3 can obtain intermediate shaping image data OB1 having an outer shape on one section of the living body tissue three-dimensional model to be shaped from the horizontal sectional data D11 as illustrated in FIG. 5 (C) and accumulates the intermediate shaping image data OB1 into the internal memory.

If the extraction process of the shaping object from such tomographic data of one tomogram ends, the image data processing apparatus 3 returns the processing to step SP3 through step SP6 described above so that it repetitively carries out processing of the process loop involving steps SP3-SP4-SP5-SP6-SP3 similarly for the tomographic data of a different tomogram from among the tomographic data of 300 tomograms. By this, the extraction process of the shaping object is successively carried out for all tomographic data.

Thus, by carrying out the extraction process, for example, for the horizontal sectional data D12 of the middle stage tomographic data illustrated in FIG. 6(C), such horizontal sectional data D12 from which intermediate shaping image data OB2 are extracted as illustrated in FIG. 7(C) can be obtained.

Further, by carrying out the extraction process of the horizontal sectional data D13 of the lower stage tomographic data illustrated in FIG. 8 (C) in a similar manner, such horizontal sectional data D13 from which intermediate shaping image data OB3 are extracted as illustrated in FIG. 9 (C) can be obtained.

Once the processing of the tomographic data of all of the 300 tomograms is completed or ends in this manner, the image data processing apparatus 3 obtains an affirmative result at step SP6 and advances to the processing to step SP7.

The processing at step SP7 involves using the intermediate shaping image data (OB1 to OB3) accumulated in the memory of the image data processing apparatus 3 by the processing at steps SP3-SP4-SP5-SP6-SP3 to cause the data to be displayed as a three-dimensional image on the display unit.

Subsequently to the displaying process of the three-dimensional image, the image data processing apparatus 3 causes the user, at step SP8, to make a decision regarding whether or not the shaping object has successfully been extracted correctly. If it is decided that the extraction from the tomographic data is not correct, then the processing returns to step SP3 described above to carry out the extraction process of the shaping object again.

On the other hand, if it is decided that the shaping object has successfully been extracted correctly, then the image data processing apparatus 3 causes, at next step SP9, the user to make a decision regarding whether or not the erasure process has successfully been carried out correctly. If a negative result is obtained, the processing returns to step SP5 described above, and the image data processing apparatus 3 carries out, at step SP5 described above, the erasure process of the tomographic data which is estimated not to have correctly undergone the erasure process.

If an affirmative result is obtained at step SP9, the image data processing apparatus 3 advances the processing to step SP10, at which it removes noise by a smoothing process to smooth the surface. Thereafter, at step SP11, the image data processing apparatus 3 causes the user to make a decision regarding whether or not all data necessary for clinical processing are prepared. If it is confirmed that all data are prepared, then the image data processing apparatus 3 returns the processing to step SP10 described above to carry out the smoothing process again.

If an affirmative result is obtained at step SP11, this signifies there is no clinical problem and the image data processing apparatus 3 then decides at step SP12 whether or not the shaping object is a blood vessel.

Here, if a negative result is obtained, the image data processing apparatus 3 advances the processing to step SP13, at which it immediately carries out a production process of tomographic shaping data S2 to be passed to the three-dimensional model production apparatus 4.

On the other hand, if an affirmative result is obtained at step SP12, this signifies that the three-dimensional images which have been processed till then require a bore, and then the image data processing apparatus 3 causes, at step SP16, the user to make a decision regarding whether or not a blood vessel wall is extracted.

If an affirmative result is obtained here, this signifies that a blood vessel is shaped already as the shaping object. At this time, the image data processing apparatus 3 advances the processing to step SP13, at which it carries out a production process of tomographic shaping data S2 having a bore.

If the shaping object is a blood vessel which does not have a lesion region, then since the three-dimensional tomographic data S1 obtained from the three-dimensional data acquisition apparatus 2 is a result of image pickup using a contrast medium, a lumen wall portion of a blood vessel surrounds the periphery with an anatomically fixed wall thickness, and therefore, an affirmative result is obtained at step SP16.

On the other hand, if a negative result is obtained at step SP16 described above, this signifies that the three-dimensional image produced by the processing till then is not completed as a blood vessel as yet.

Therefore, the image data processing apparatus 3 causes the processing to proceed to step SP17, at which it causes the user to write image data of a lumen wall of a predetermined wall thickness regarding the three-dimensional image produced till then and then displays the three-dimensional image.

Here, the wall thickness of the blood vessel wall is determined in accordance with conditions of the blood vessel region of the shaping object based on the fact that anatomically a thick blood vessel has a great wall thickness while a thin blood vessel has a small wall thickness.

Then, the image data processing apparatus 3 advances the processing to step SP18, at which it causes the user to make a decision regarding whether or not the blood vessel has some collapse or dissociation.

If a negative result is obtained here, then the image data processing apparatus 3 corrects the fault at step SP19 and then returns the processing to step SP18 described above. Consequently, the image data processing apparatus 3 repeats the correction process until after the three-dimensional image of the blood vessel becomes free from any fault.

Thus, the image data processing apparatus 3 ends the production process of the tomographic shaping data S2 based on the three-dimensional tomographic data S1 from the three-dimensional data acquisition apparatus 2 at step SP13 and then sends the tomographic shaping data S2 to the three-dimensional model production apparatus 4, which is an optical shaping apparatus, at step SP14 so that a shaping process is carried out. Consequently, the shaping data production processing procedure RT0 ends at step SP15.

(3) Correction Process of Fault

The following cases are available as the correction process of a fault at steps SP18-SP19-SP18 of the shaping data production processing procedure RT0 described above.

(3-1) Case in which Thrombus Exists in Aortic Aneurysm

When three-dimensional tomographic data S1 which include a thrombus 13 because an aortic aneurysm 12 appears on an aorta 11 as shown in FIG. 10 is supplied, the image data processing apparatus 3 extracts, at step SP4 of the shaping data production processing procedure RT0, a boundary between a shaping object and the other tissue. Consequently, as three-dimensional tomographic data 15 of the aorta 11 at the height levels V1, V2, V3 and V4, outer surfaces 11A1, 11A2, 11A3 and 11A4 which are extraordinarily swollen at the portion of the aortic aneurysm 12 are extracted.

Then at step SP17 described above, the image data processing apparatus 3 causes the user to place wall thicknesses of predetermined lumen walls 11B1, 11B2, 11B3 and 11B4 into the inner side of the outer surfaces 11A1, 11A2, 11A3 and 11A4 of the aorta 11 and then displays a three-dimensional image of the aorta 11 on the display unit.

Here, the wall thicknesses of the lumen walls 11B1, 11B2, 11B3 and 11B4 are selectively set to comparatively great thicknesses because the aorta 11 is a thick blood vessel.

Further, since blood flow portions 11C1, 11C2, 11C3 and 11C4 of the bore at the lumen walls 11B1, 11B2, 11B3 and 11B4 include a contrast medium therein, they are filled with image data brighter than those of the lumen walls 11B1, 11B2, 11B3 and 11B4.

Therefore, such image data are obtained which represent that, while the blood flow portions 11C1 and 11C4 at the height levels V1 and V4 at which the thrombus 13 does not exist contact as a whole the inner face of the lumen walls 11B1 and 11B4, the blood flow portions 11C2 and 11C3 at which the thrombus 13 exists do not contact the lumen walls 11B2 and 11B3 at the thrombus portions 11D2 and 11D3 and an image portion having a density substantially proximate to the density of the aorta 11 is interposed between them.

Thus, when an image process is carried out selecting an aorta as a shaping object, the image data processing apparatus 3 produces a decision result at step SP18 that the blood vessel has dissociation.

Figure 11:
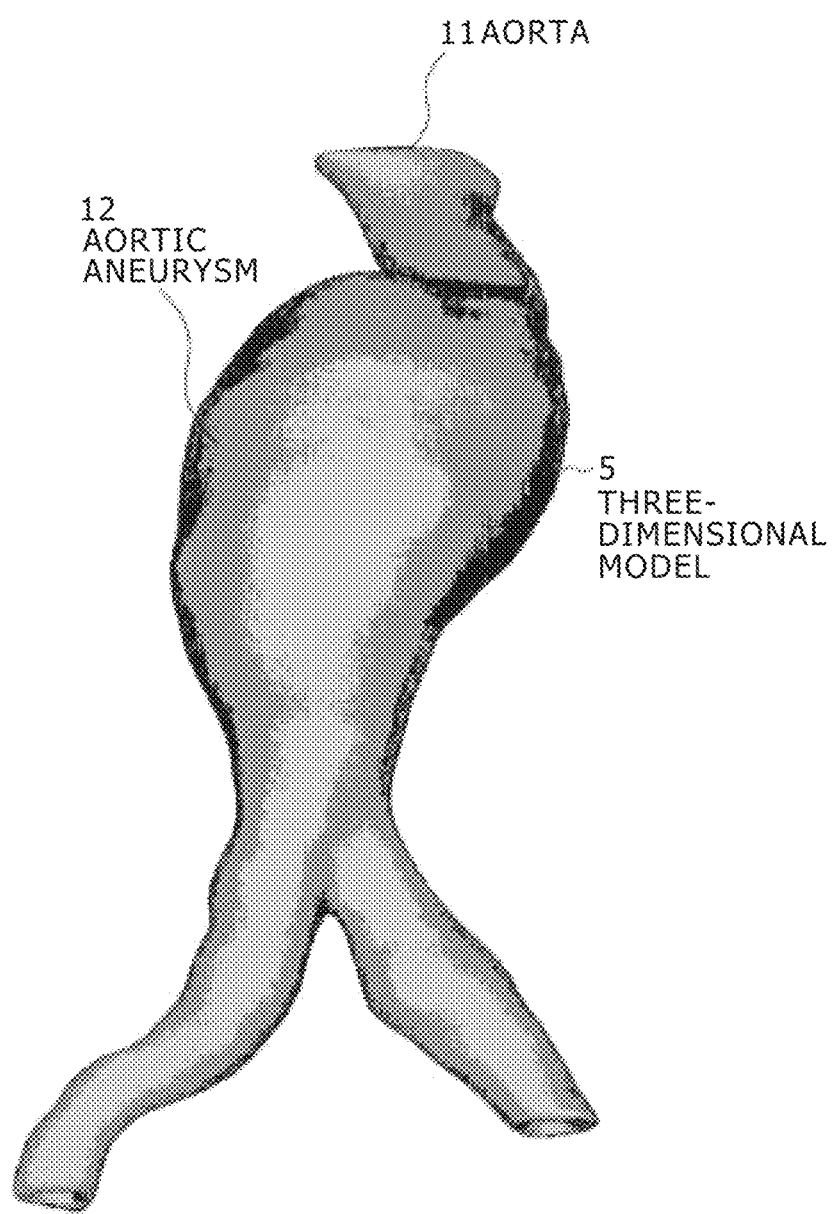
FIG. 11 is a side elevational view showing a produced three-dimensional model.
Figure 12:
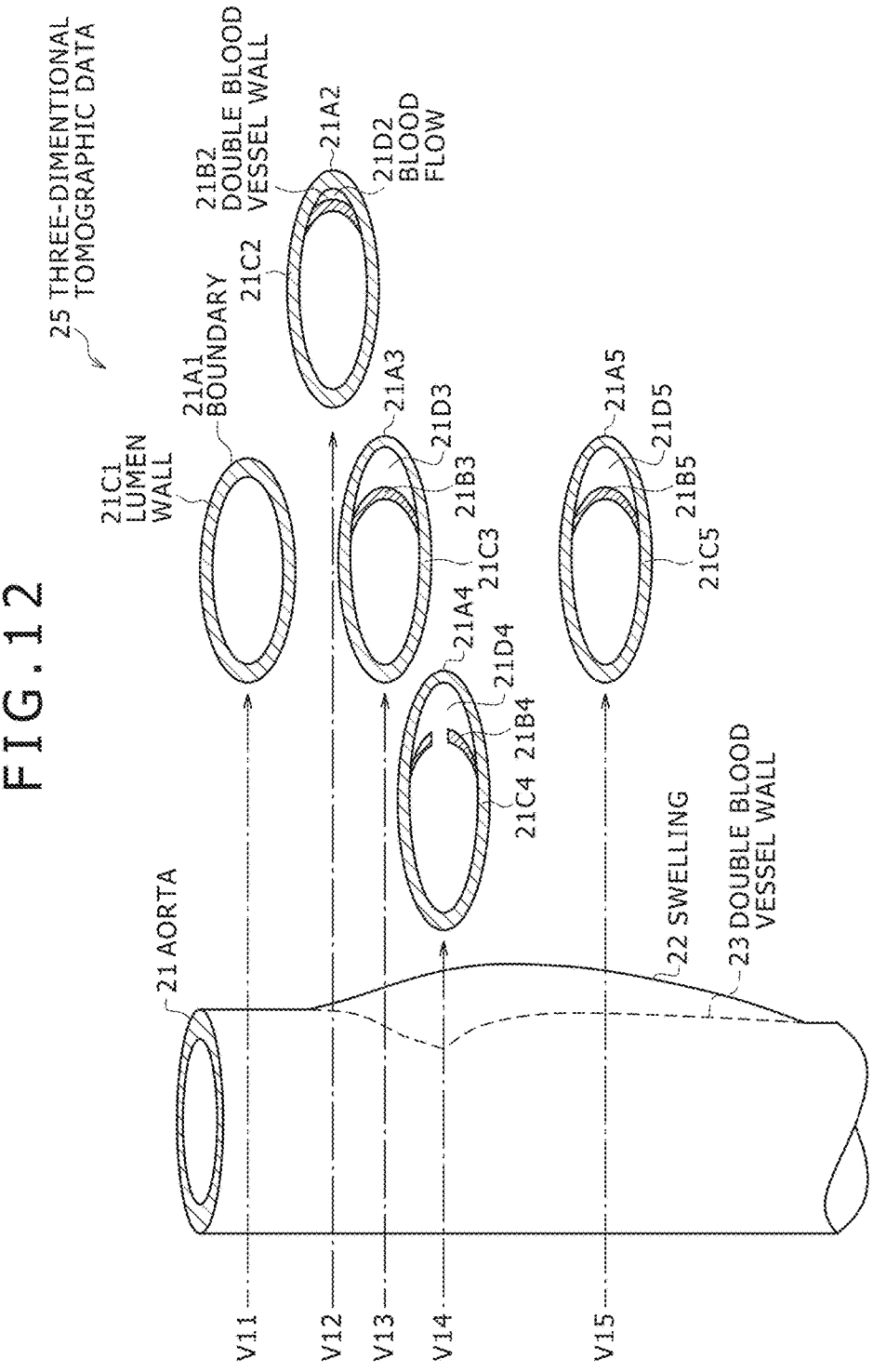
FIG. 12 is a schematic view illustrating a process of image data where an aorta dissociation is found.

Therefore, if, at the fault correction step SP19, the tomographic shaping data S2 corrected such that the thrombus portions 11D2 and 11D3 make an image cut away from that of the lumen walls 11B2 and 11B3 of the aorta 11 are produced, then the three-dimensional model 5 obtained from the three-dimensional model production apparatus 4 reconstructs the aorta 11 (which has an internal structure wherein the thrombus 13 exists in the inside of the aortic aneurysm 12) having the aortic aneurysm 12 as shown in FIG. 11.

(3-2) Case where Aorta Dissociation Exits

In the case in which an aorta 21 which is normal at a height level V11 according to anatomical information has a swelling 22 at height levels V12 to V15, if a boundary is extracted between a shaping object and the other tissue at step SP4 of the shaping data production processing procedure RT0 from three-dimensional tomographic data 25 obtained based on the three-dimensional tomographic data S1 obtained from the three-dimensional data acquisition apparatus 2, then boundaries 21A1, 21A2, 21A3, 21A4 and 21A5 are obtained.

Then, when lumen walls 21C1, 21C2, 21C3, 21C4 and 21C5 of the aorta 11 are inputted at step SP17 described hereinabove, if double blood vessel walls 21B2, 21B3, 21B4 and 21B5 exist in the tomographic data at the height levels V12, V13, V14 and V15, then the image data processing apparatus 3 decides at step SP18 that the blood vessel has collapse or dissociation. Therefore, at step SP19, a correction process of the fault is carried out.

In the case of the present embodiment, it can be confirmed that the blood flow portions 21D2, 21D3, 21D4 and 21D5 exist between the double blood vessel walls 21B2, 21B3, 21B4 and 21B5 and the lumen walls 21C2, 21C3, 21C4 and 21C5, and according to circumstances, the double blood vessel walls 21B2, 21B3, 21B4 and 21B5 may partly be cut such that they look in such manner as to hang down like a flap the double blood vessel wall 21B4.

If such a blood vessel as just described can be confirmed at step SP18, then a three-dimensional model can be produced by reconstructing without being lost blood vessel information which the three-dimensional tomographic data 25 have.

(3-3) Case in which Branch of Blood Vessel Exists

Figure 13:
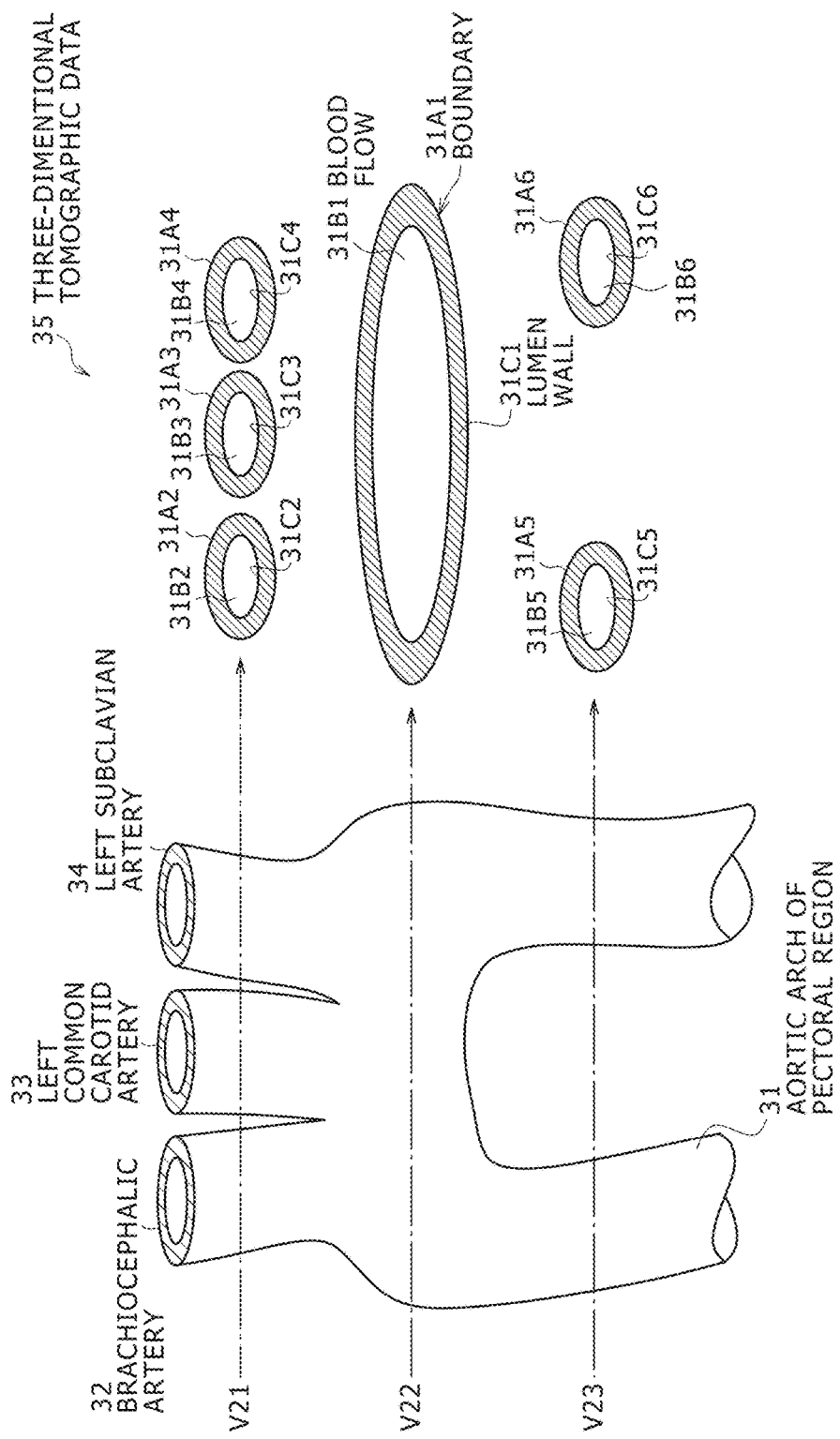
FIG. 13 is a schematic view illustrating a process of image data where bifurcation of a blood vessel is found.

As shown in FIG. 13, if three-dimensional tomographic data S1 regarding an aortic arch 31 of the pectoral region are taken in from the three-dimensional data acquisition apparatus 2, then when the image data processing apparatus 3 extracts a boundary between a shaping object and the other tissue at step SP4 of the shaping data production processing procedure RT0, a boundary 31A1 of a large elliptical shape is extracted at the height level V22. However, at the height level V21 higher than the body portion, boundaries 31A2, 31A3 and 31A4 of a small elliptical shape corresponding to a brachiocephalic artery 32, a left common carotid artery 33 and a left subclavian artery 34 are extracted and boundaries 31A5 and 31A6 corresponding to two branches are extracted at the height level V23 on the lower side of the boundary 31A1.

When such three-dimensional tomographic data 35 of a shaping object image are obtained, since bright image data exist in the inside of the boundaries 31A1 to 31A6 due to a contrast medium included in the blood flows 31B1 to 31B6, the lumen walls 31C1 to 31C6 are extracted. Thus, if it is confirmed at step SP6 described hereinabove that there is no anatomical contradiction, then an affirmative result is obtained at step SP16 for deciding whether or not a blood vessel wall is extracted. Therefore, inputting of a wall thickness at step SP17 is omitted, and the processing advances to the shaping data production processing step SP13.

By the configuration described above, the shaping data production processing procedure RT0 can be simplified by the omission of the processing step.

Figure 14:
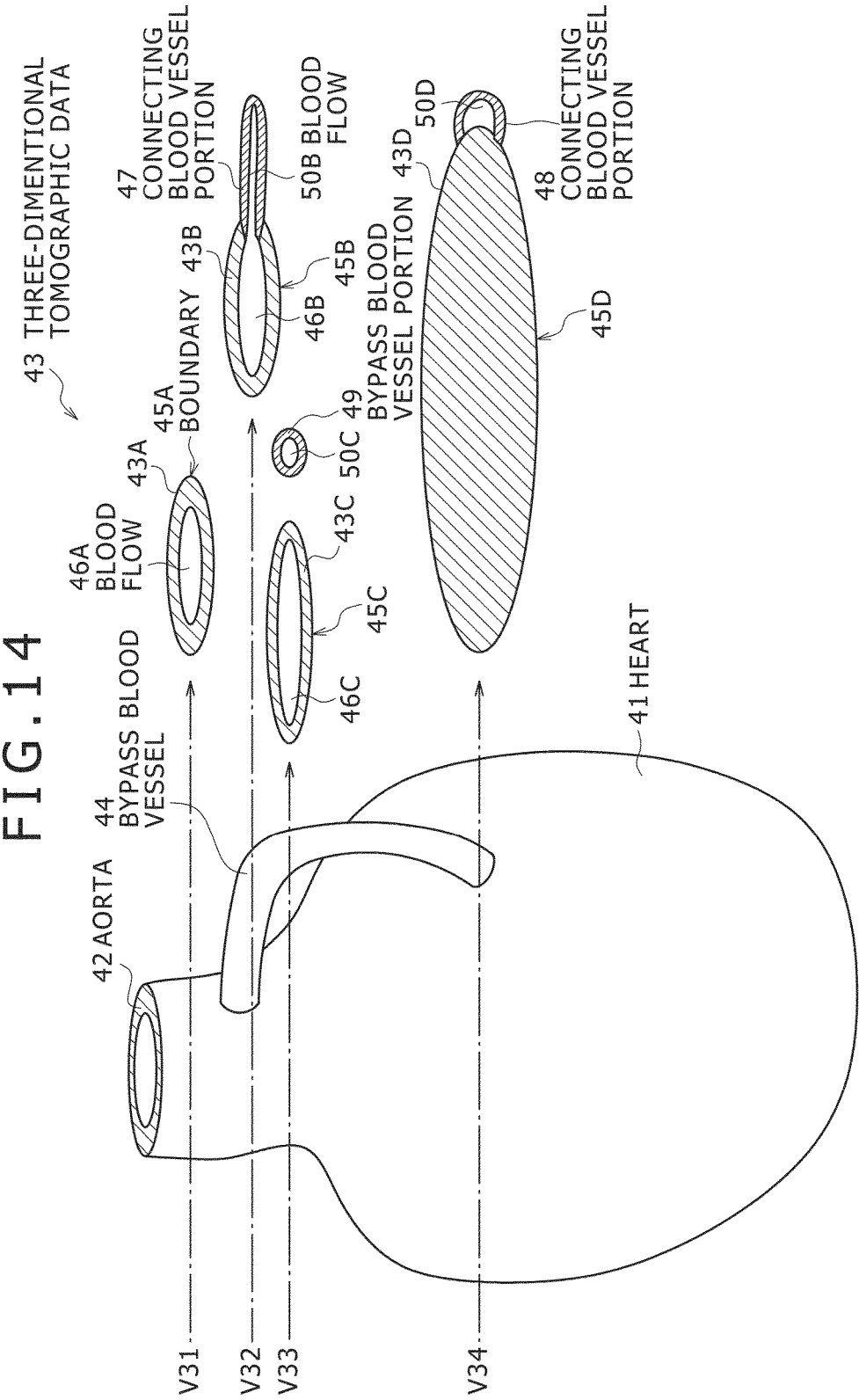
FIG. 14 is a schematic view illustrating an image process where a blood vessel which should not originally exist is found.

(3-4) Case in which Branch of Blood Vessel which should not Originally Exist Exits Referring to FIG. 14, an image data process is illustrated where, in the case wherein a region in which an aorta 42 extends from the heart 41 is determined as a shaping object, lumen walls 43A, 43B and 43C are obtained as three-dimensional tomographic data 43 on height levels V31, V32 and V33 of the portion of the aorta 42 and a tomographic image 43D is obtained on a height level V34 of the heart 41 and three-dimensional tomographic data S1 including a shaping object which includes a bypass blood vessel 44 which should not anatomically exist are supplied. In this instance, the image data processing apparatus 3 can extract boundaries 45A, 45B and 45C on the height levels V31, V32 and V33 by extracting the boundary between the shaping object and the other tissue at step SP4 of the shaping data production processing procedure RT0.

Together with this, the image data processing apparatus 3 extracts a boundary 45D on the height level V34 between the heart 41 as the shaping object and the other tissue at step SP4 of the shaping data production processing procedure RT0 similarly.

Here, while, on the height levels V31, V32 and V33, picked up images of the blood flows 46A, 46B and 46C are obtained on the inner side of the lumen walls 43A, 43B and 43C, on the height level V34, data regarding the portion corresponding to the blood flow are not produced.

While the process of image data described above is carried out in accordance with anatomic information, in the case of the shaping object of FIG. 14, processing of image data regarding the bypass blood vessel 44 is carried out in addition.

In other words, the tomographic data on the height level V32 includes a connecting blood vessel portion 47 in regard to a connecting portion between the aorta 42 and the bypass blood vessel 44.

Another connecting blood vessel portion 48 is included in a portion at which the bypass blood vessel 44 is connected to the heart 41 on the height level V34.

Furthermore, the three-dimensional tomographic data 43 include a bypass blood vessel portion 49 in the neighborhood of the lumen wall 43C of the aorta on the height level V33.

The connecting blood vessel portions 47 and 48 regarding the bypass blood vessel 44 and the bypass blood vessel portion 49 can be decided as blood vessels because, although it cannot be anatomically forecast, that the blood flows 50B and 50C as well as 50D exist in the blood vessel portions is displayed as an image of the contrast medium.

Thus, since, as regards the bypass blood vessel 44, tomographic data of the same in the heightwise direction from the connecting blood vessel portion 47 to the connecting blood vessel portion 48 through the bypass blood vessel portion 49 are produced continuously, the image data processing apparatus 3 decides from the specificity of the tomographic data that the bypass blood vessel 44 exists, and carries out an image process of the bypass blood vessel 44.

(4) Admission Port Member of Surgical Instrument

The three-dimensional model 5 shown in FIG. 11 is obtained from the tomographic shaping data S2 produced by the image data processing apparatus 3 using the three-dimensional model production apparatus 4 and reconstructs not only the external shape of the same but also the structure of a bore.

Therefore, it is highly effective if it is possible to attempt such a clinical technique as to insert a surgical instrument for operating a thrombus 13 (FIG. 10) existing in a bore of the aortic aneurysm 12 utilizing the three-dimensional model to a position of the aortic aneurysm 12.

Figure 15:
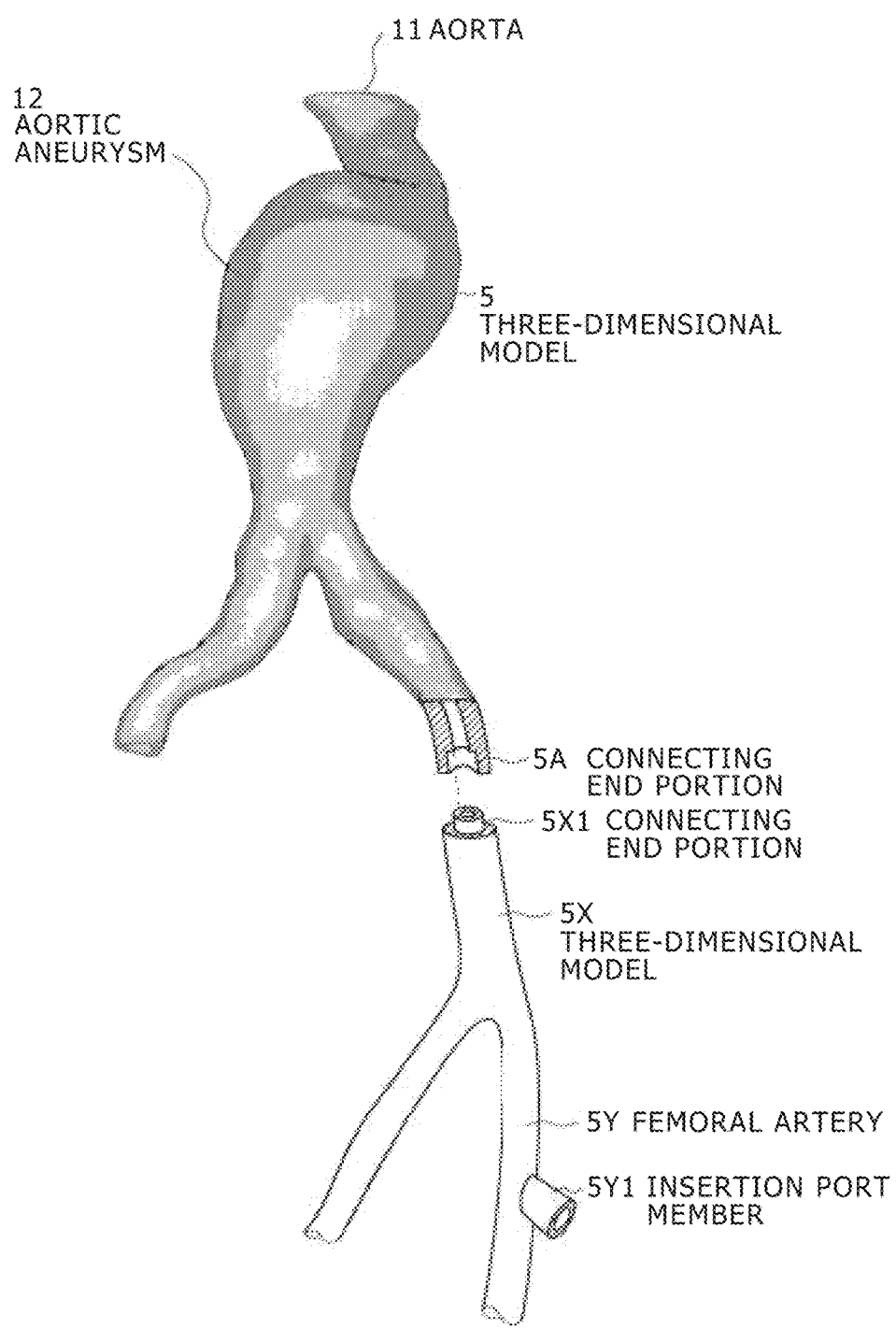
FIG. 15 is a side elevational view illustrating a three-dimensional model which is configured so that an operation instrument can be inserted.

As a tool investigated before such a surgical technique is carried out clinically, as shown in FIG. 15, three-dimensional tomographic data S1 of a femoral artery 5Y positioned far away from the aorta 11 are obtained from the three-dimensional data acquisition apparatus 2 to produce tomographic shaping data S2 using the shaping data production processing procedure RT0 illustrated in FIGS. 2 and 3. Then, the tomographic shaping data S2 are processed by the three-dimensional model production apparatus 4 to reconstruct a femoral artery 5Y as a three-dimensional model 5X.

Here, since the femoral artery 5Y is positioned surgically in a spaced relationship from the aortic aneurysm 12 of the three-dimensional model 5, the three-dimensional model 5X is prepared as a part connecting to a part of the three-dimensional model 5 separately from the three-dimensional model 5 which includes the aortic aneurysm 12.

Thereupon, the image data processing apparatus 3 carries out a processing operation so that an insertion port member 5Y1 which reconstructs an insertion port is provided on the three-dimensional model 5X in a corresponding relationship to the position of a femoral region at which the insertion port is provided in order to clinically insert a catheter into a femoral artery to feed into the aortic aneurysm.

Figure 16:
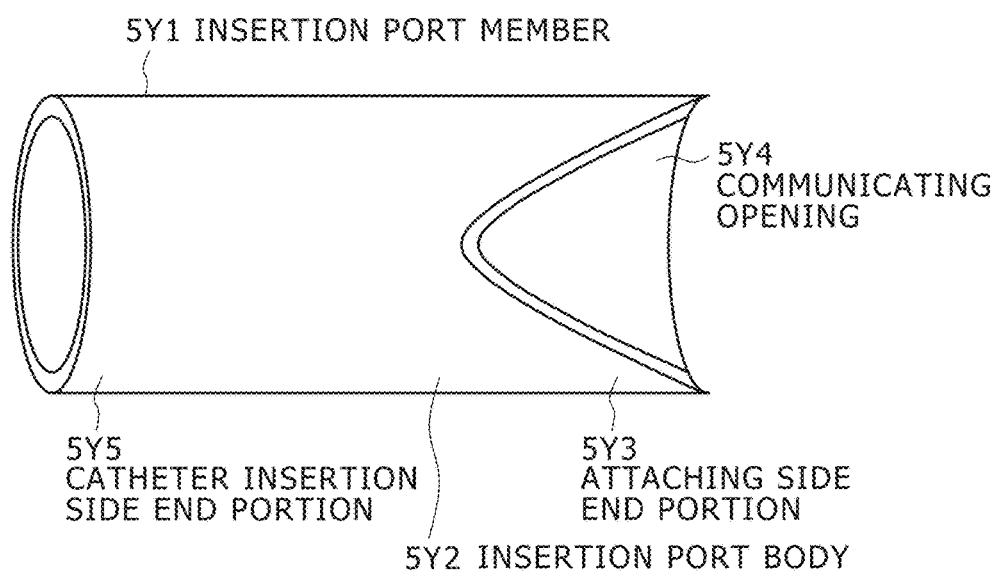
FIG. 16 is a side elevational view showing an insertion port in FIG. 15.

The insertion port member 5Y1 which is used clinically has a configuration shown in FIG. 16.

The insertion port member 5Y1 has an insertion port body 5Y2 having a generally cylindrical shape, and a communicating opening 5Y4 communicating with a bore of the femoral artery is cut away at a side portion of an attaching side end portion 5Y3 to the femoral artery. Consequently, the insertion port member 5Y1 is attached obliquely to the communicating opening 5Y4 such that it extends along the femoral artery.

Thus, a catheter is inserted into an opening of a circular sectional shape of a catheter insertion side end portion 5Y5, and a distal end of the catheter is inserted into the femoral artery through the communicating opening 5Y4.

Here, since the technique of inserting a catheter after the insertion port member 5Y1 is attached is carried out as a series of operations, it is made possible to attempt an insertion operation of a catheter prior to the surgical operation using the three-dimensional models 5 and 5X with regard to the installation direction and the installation position with respect to the femoral artery.

The three-dimensional model 5X is produced by adding tomographic data of the insertion port member 5Y1 to tomographic data produced by the image data processing apparatus 3 executing the shaping data production processing procedure RT0 of FIGS. 2 and 3 with regard to the three-dimensional tomographic data S1 obtained from the femoral region by the three-dimensional data acquisition apparatus 2.

At a connecting end portion 5A of the three-dimensional model 5 to the three-dimensional model 5X which are formed as different parts from each other, a fitting portion 5A1 configured as a cylindrical recessed portion is formed, and a circumferential line portion of the connecting end portion 5A is cut in a thick portion of a lumen wall 5A2.

In contrast, a projection 5X2 configured as a cylindrical projection is formed on the connecting end portion 5X1 of the three-dimensional model 5X, and a circumferential portion of the projection 5X2 is configured such that an outer circumferential portion of a thick portion of a lumen wall 5X3 is cut away.

A bore 5A3 of the connecting end portion 5A of the three-dimensional model 5 and a bore 5X4 of a connecting end portion 5X1 of the three-dimensional model 5X have inner diameters equal to each other.

Figure 17:
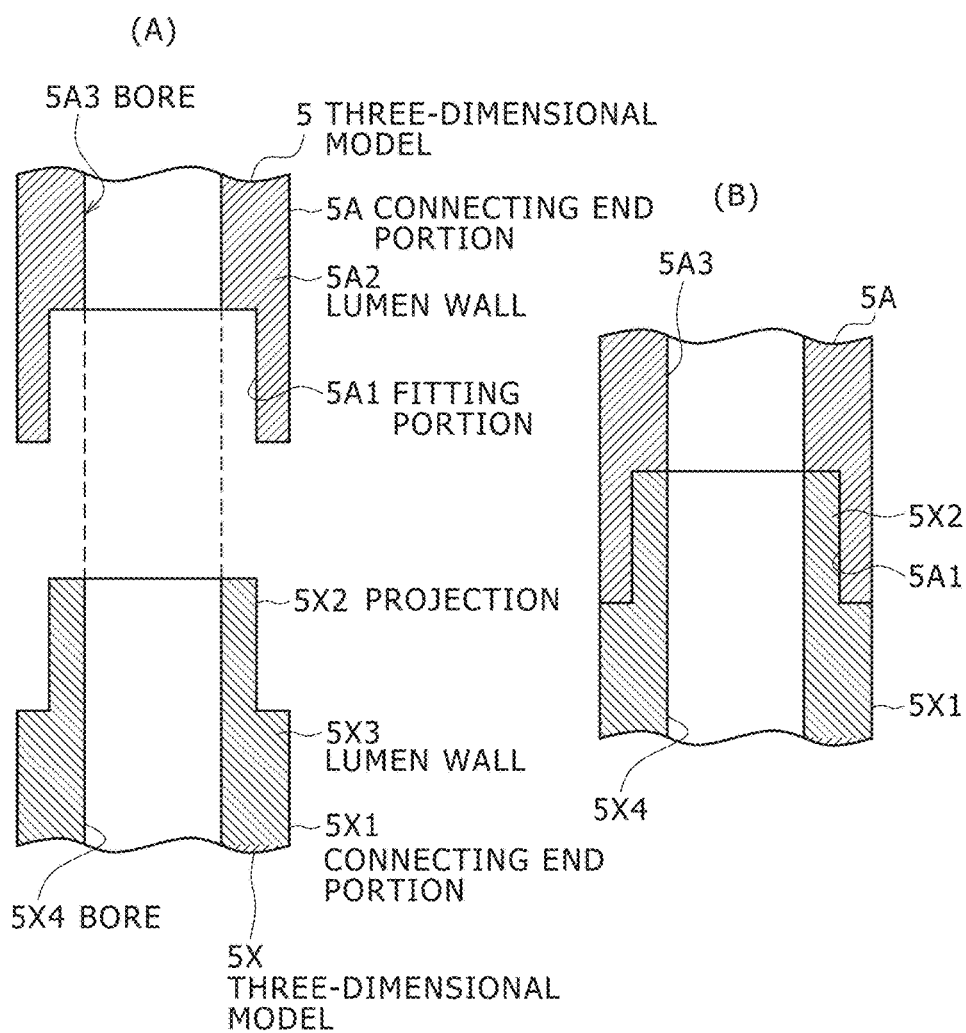
FIG. 17 is sectional views showing a configuration of a connection end portion in FIG. 15.

As shown in FIG. 17(B), the projection 5X2 is configured such that it can be fitted in the fitting portion 5A1 without play, and when a catheter as a surgical instrument inserted in the bore 5X4 of the three-dimensional model 5X passes the boundary of the fitting portion 5A1 from the projection 5X2, since no offset exists at the boundary, the distal end of the catheter can move from the bore 5X4 of the connecting end portion 5X1 to the bore 5A3 of the connecting end portion 5A.

Thus, a three-dimensional model having a bore structure the same as a clinical bore structure from the aortic aneurysm 12 to the insertion port member 5Y1 of the femoral artery 5Y positioned in a spaced relationship from the aortic aneurysm 12 is reconstructed by connecting the three-dimensional models 5 and 5X which are different parts from each other. By this, the catheter insertion technique from the insertion port member 5Y1 can be attempted prior to carrying out the same in actual clinic use.

As a result, if the installation position or the installation angle of the insertion port member 5Y1 is inappropriate from the appearance position of an aortic aneurysm in the bore of the aorta 11, this can be confirmed in advance. Thereupon, if a plurality of three-dimensional models 5X which are different in the installation position and the installation angle in accordance with different conditions are prepared in advance and one of them is connected to the connecting end portion 5A of the three-dimensional model 5 having the aortic aneurysm 12 through the connecting end portion 5X1, then further optimum installation conditions of the insertion port member 5Y1 can be confirmed.

(5) Operation and Effect of the Disclosure

With the configuration described above, a three-dimensional model which reconstructs a living body tissue having a bore such as a blood vessel can be obtained utilizing the fact that the three-dimensional tomographic data S1 obtained from the three-dimensional data acquisition apparatus 2 includes image information of a three-dimensional position in the human body.

Thus, a three-dimensional model as a tool with which a state of a tissue in the body including a lesion region or a prior surgical operation mark can be forecast sufficiently can be obtained appropriately.

Together with this, by providing an insertion port member with which a surgical instrument can be inserted into a blood vessel on a three-dimensional model, a clinical technique can be attempted in advance, and consequently, a surgical operation can be carried out more readily.

(6) Flow Indicator

Figure 18:
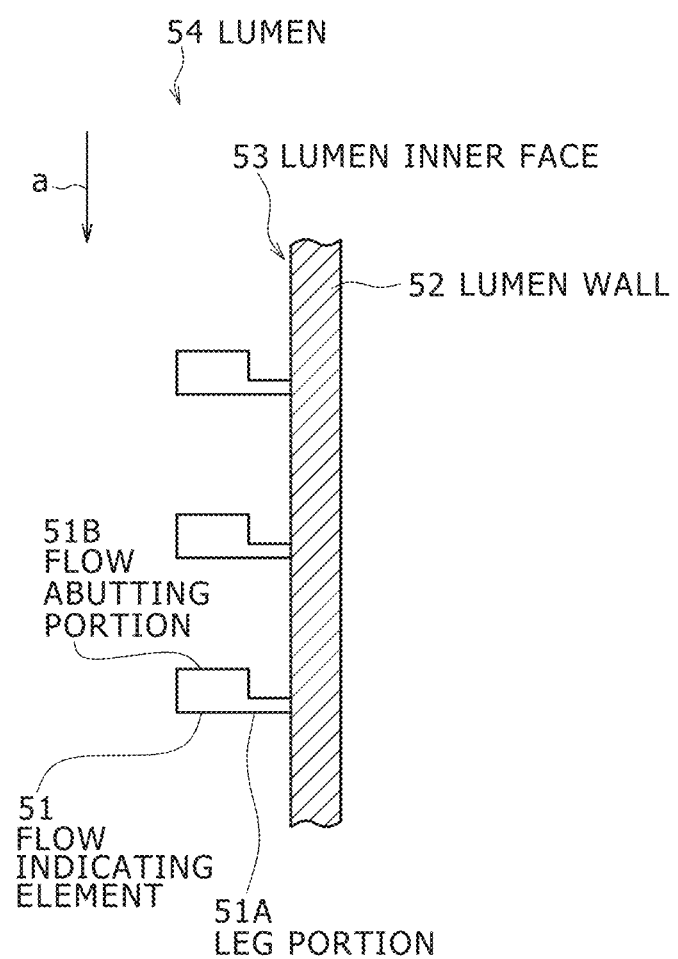
FIG. 18 is a partial sectional view showing a three-dimensional model wherein a flow indicating element projects from a lumen wall.

Such flow indicating elements 51 as shown in FIG. 18 are added to a living body tissue having a tube-like lumen, for example, a blood vessel, in the tomographic shaping data S2 produced by the image data processing apparatus 3 in such a manner as described hereinabove with reference to FIGS. 10 to 14.

The flow indicating elements 51 are implanted at suitable intervals for visual observation on a lumen inner face 53 of a lumen wall 52 such that they project into the bore space.

In the case of the present embodiment, the flow indicating elements 51 are small pieces (cantilever pieces) each in the form of a thin plate and have a flexible thin leg portion 51A and a flow abutting portion 51B of a greater width formed at an end portion of the leg portion 51A.

Thus, when fluid (pseudo fluid corresponding to the blood) indicated by an arrow mark a flows in a lumen 54 surrounded by the lumen wall 52 and is brought into abutment with the flow abutting portion 51B of a flow indicating element 51 projecting from the lumen inner face 53, since the flow abutting portion 51B is formed with a greater width, it is acted upon by force from the fluid such that it is inclined or is turned so as to change the direction.

Thus, since the flow indicating element 51 changes its state in response to a manner in which the fluid flowing in the lumen 54 surrounded by the tube-shaped lumen wall 52 flows, by visually inspecting the variation of the flow indicating elements 51, the flowing manner of the fluid can be discriminated.

Figure 19:
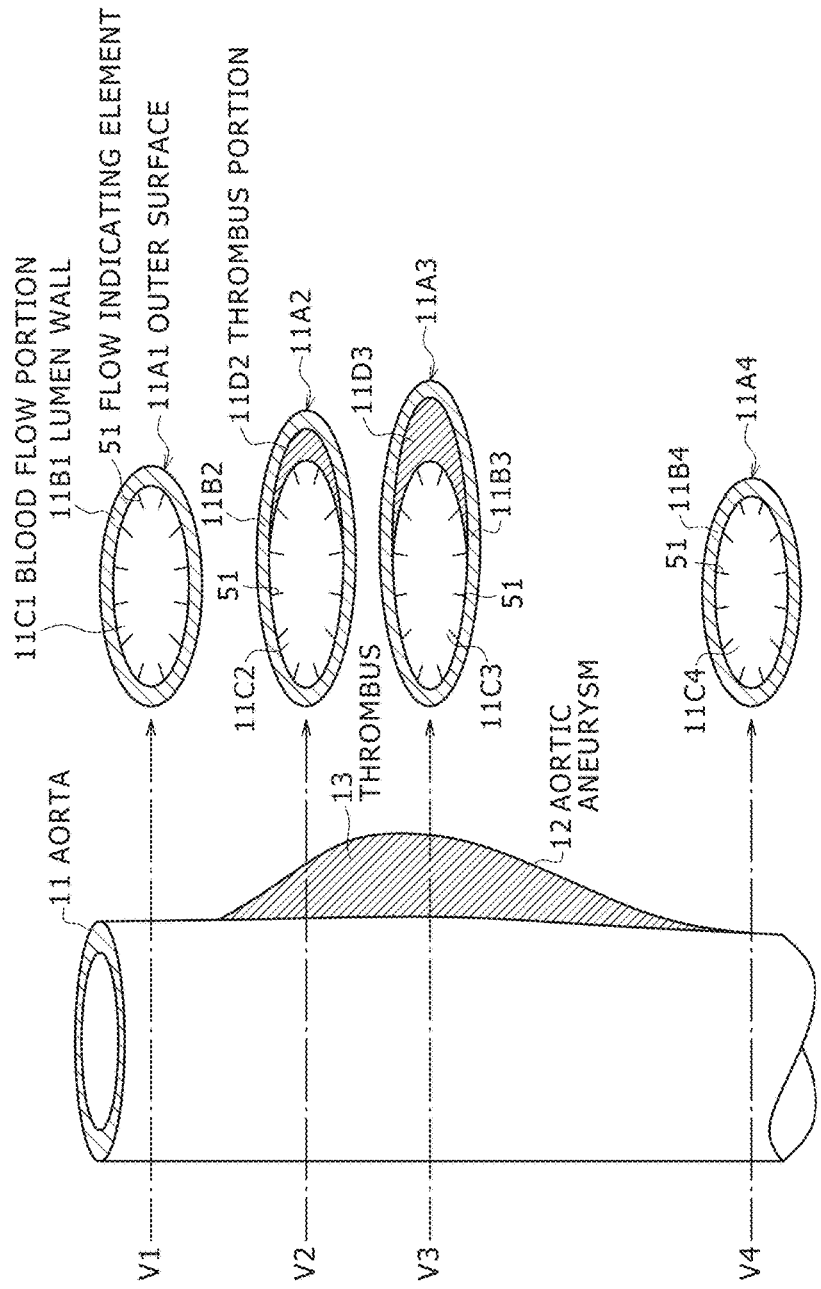
FIG. 19 is a schematic view illustrating a case wherein a flow indicating element is applied where a thrombus exists in an aortic aneurysm.

If this flow indicating element 51 is applied to a case in which a thrombus exists in an aortic aneurysm described hereinabove, for example, with reference to FIG. 10, then a flowing manner of the blood in the aortic aneurysm 12 in which the thrombus 13 exists can be confirmed from a flowing manner of the fluid which can be visually inspected from the flow indicating elements 51 of the lumen walls 11B1 and 11B4 in which no thrombus exists and a flowing manner of the fluid which can be discriminated by visually inspecting the flow indicating elements 51 of the lumen walls 11B2 and 11B3 in which the thrombus 13 exists as shown in FIG. 19.

With the configuration described above, since an influence of the fluid flowing in a lumen surrounded by a lumen wall can be visually inspected from the flow indicating elements 51 projecting from the lumen inner face 53 of the lumen wall 52, information for diagnosis of a relationship between a flowing manner of fluid and a lesion region can be provided.

In fact, although the tomographic shaping data S2 including three-dimensional tomographic data where the flow indicating elements 51 are projected on the lumen wall 52 are produced as a three-dimensional model 5 by being supplied from the image data processing apparatus 3 to the three-dimensional model production apparatus 4, when the flow indicating elements 51 are produced from the three-dimensional tomographic data, it is effective to apply an active energy effectiveness resin as disclosed in Japanese Patent Laid-Open No. 2006-2087.

In the embodiment of FIG. 18, the flow indicating elements 51 are shaped such that a flow abutting portion 51B of a greater width is formed at an end portion (free end portion) of a leg portion 51A, the shape of the flow indicating element 51 is not limited to this, but flow indicators of various shapes can be applied. What is important is that small pieces in the form of a thin plate project into the lumen 54 of the lumen wall 52 and are yielded by a flow of fluid a.

(7) Motion Detection of Lumen Wall (7-1) Detection by Motion Detector

As described above, the image data processing apparatus 3 can obtain a three-dimensional model 5 by carrying out an image process of the three-dimensional tomographic data S1 acquired from the three-dimensional data acquisition apparatus 2 to produce tomographic shaping data S2 regarding a living body tissue to be targeted and then supplying the tomographic shaping data S2 to the three-dimensional model production apparatus 4.

Figure 20:
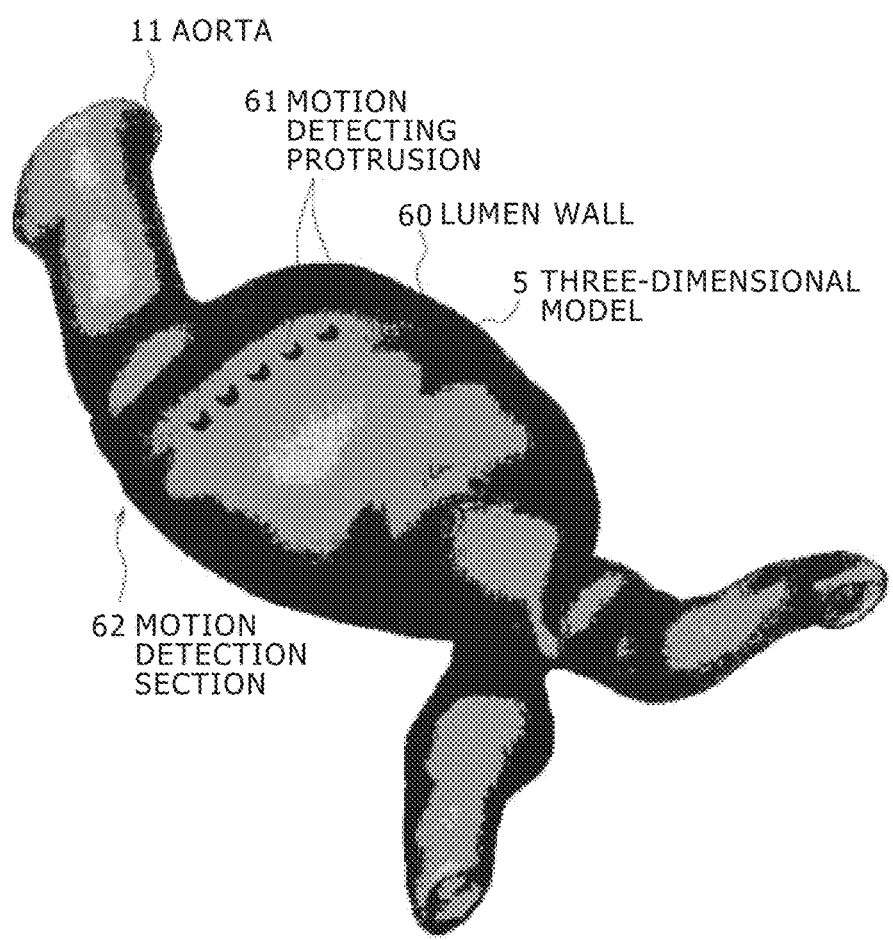
FIG. 20 is a perspective view showing a motion detection section provided on a three-dimensional model.
Figure 21:
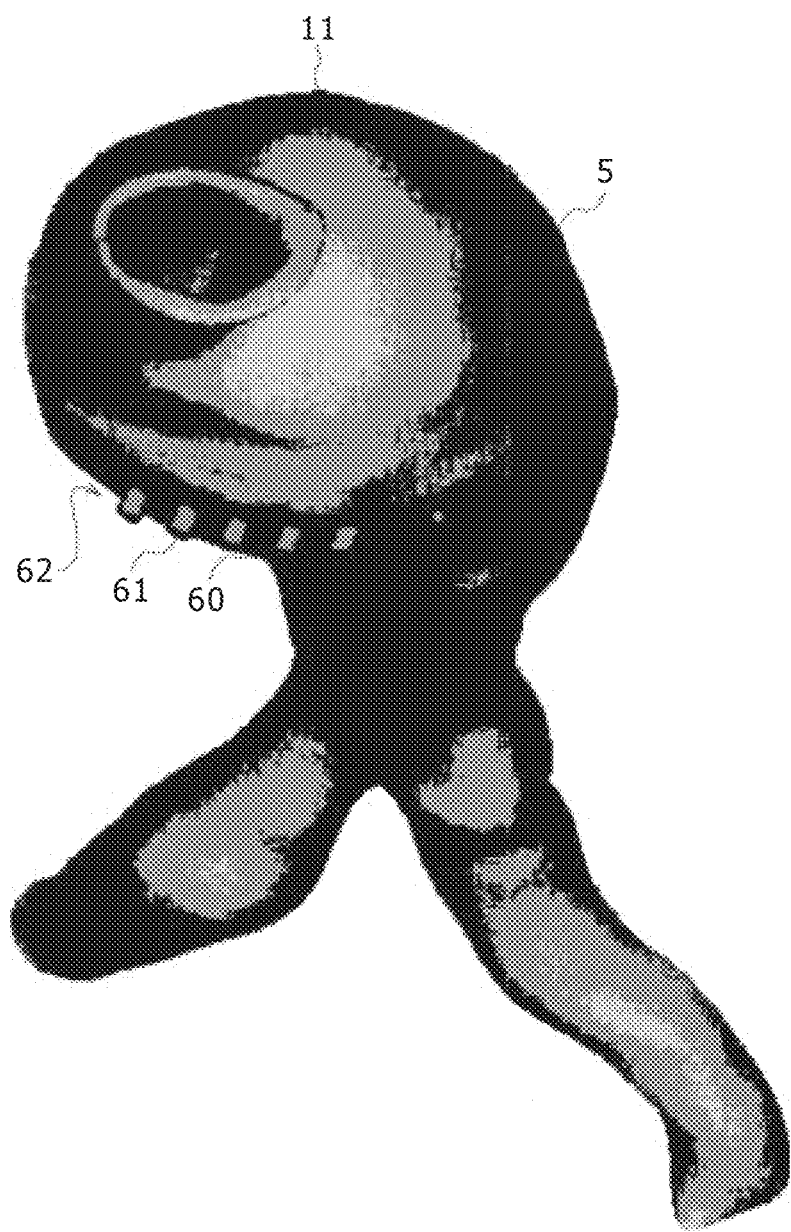
FIG. 21 is a perspective view showing the motion detection section as viewed from a different direction from that in FIG. 20.

If such a three-dimensional model 5 as shown in FIGS. 20 and 21 is reconstructed as a three-dimensional model which reconstructs the aorta 11 including a lesion region of the aortic aneurysm 12 in which a thrombus 13 exists as described hereinabove with reference to FIGS. 10 and 11, a motion detection section 62 having a plurality of motion detecting protrusions 61 arrayed thereon is provided on an outer surface of the lumen wall 60 of the three-dimensional model 5. The motion detection section 62 comprising the plurality of motion detecting protrusions 61 constitutes one embodiment of means for detecting movement (displacement) of the lumen wall to allow measurement of pressure in the lumen surrounded by the lumen wall (means for measuring pressure).

Figure 22:
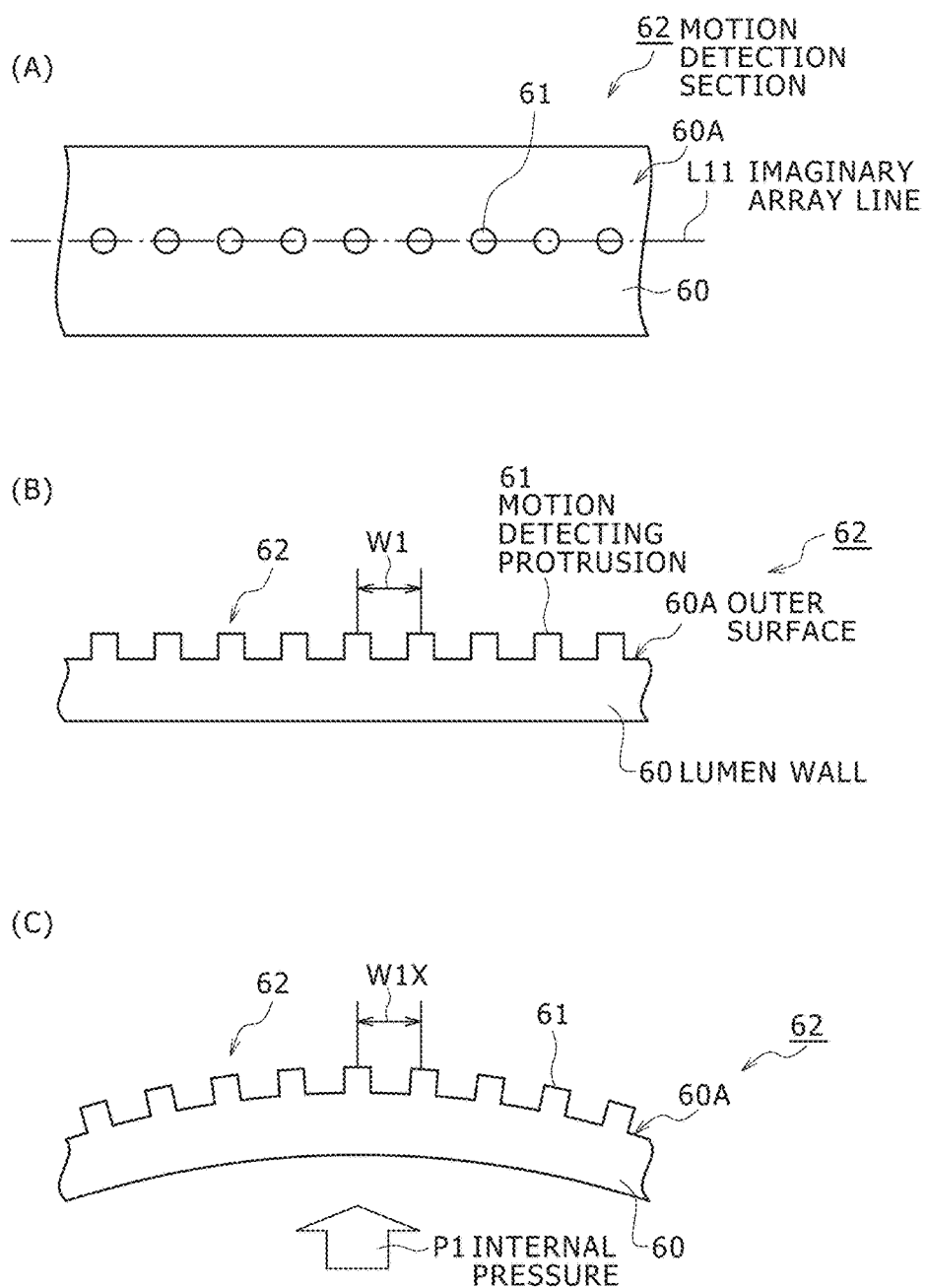
FIG. 22 is schematic views illustrating motion detection operation by a motion detecting protrusion.

In the case of the present embodiment, on the motion detection section 62, a plurality of motion detecting protrusions 61 having a cylindrical shape project from the lumen wall 60 of the aorta 11 and are arrayed such that they have a mutual distance W1 therebetween on an imaginary array line L11 as shown in FIGS. 22(A) and 22(B).

In the configuration described above, if pressure is applied to the lumen surrounded by the lumen wall 60, then the lumen wall 60 is acted upon by internal pressure P1 and swollen outwardly as shown in FIG. 22(C).

At this time, the mutual distance W1 between the motion detecting protrusions 61 which configure the motion detection section 62 increases to W1X because the outer surface 60A of the lumen wall 60 moves in a direction in which the distance between the motion detecting protrusions 61 increases as the lumen wall 60 is swollen in FIG. 22(C)) from the FIG. 22(B) state before the pressure is applied.

The variation of the distance between the motion detecting protrusions 61 corresponds to the degree of swelling of the lumen wall 60 and accordingly to the magnitude of the internal pressure P1.

If the internal pressure P1 is removed in this state, then since the lumen wall 60 restores its original state, the elongation of the outer surface 60A disappears and the original mutual distance W1 is restored.

With the configuration described above, by visually inspecting and confirming the variation of the mutual distance W1 of the motion detecting protrusions 61 of the motion detection section 62 provided on the outer surface 60A of the lumen wall 60, the user can find a variation of the swelling manner of the lumen wall 60 and accordingly a variation of the magnitude of the internal pressure P1.

Accordingly, where a lesion region also exists on the lumen wall 60, by observing a variation of the mutual distance W1 of the motion detecting protrusions 61, movement of the lumen wall 60 with respect to the internal pressure P1 where the lumen wall 60 has the lesion region can be grasped.

(7-2) Detection by Distortion Detection Element

FIG. 23 shows a motion detection section 66 which can detect distortion applied to the lumen wall 60 as an electric signal by distortion detection elements 65. The motion detection section 66 comprising the distortion detection elements 65 constitutes another embodiment of means for detecting movement (displacement) of the lumen wall to allow measurement of pressure in the lumen surrounded by the lumen wall (means for measuring pressure).

In this instance, a plurality of distortion detecting holes 60B are perforated on an imaginary array line L12 on the outer surface 60A of the lumen wall 60, and the distortion detection elements 65 are force fitted in the distortion detecting holes 60B as shown in FIG. 23(C) thereby to configure the motion detection section 66.

According to the configuration of FIG. 23, if the pressure in the lumen surrounded by the lumen wall 60 increases to such a degree that the lumen wall 60 is swollen even a little, the wall face of the distortion detecting holes 60B is displaced to reduce the pressure to the distortion detection elements 65 fitted in the distortion detecting holes 60B. Consequently, an electric detection output which varies in response to the applied pressure can be obtained from the distortion detection elements 65.

Thus, with the configuration of FIG. 23, such a motion detection section 66 which can detect the pressure in a lumen as a quantitative numerical value can be obtained.

(7-3) Detection by Pressure Sensing Mechanism

Figure 24:
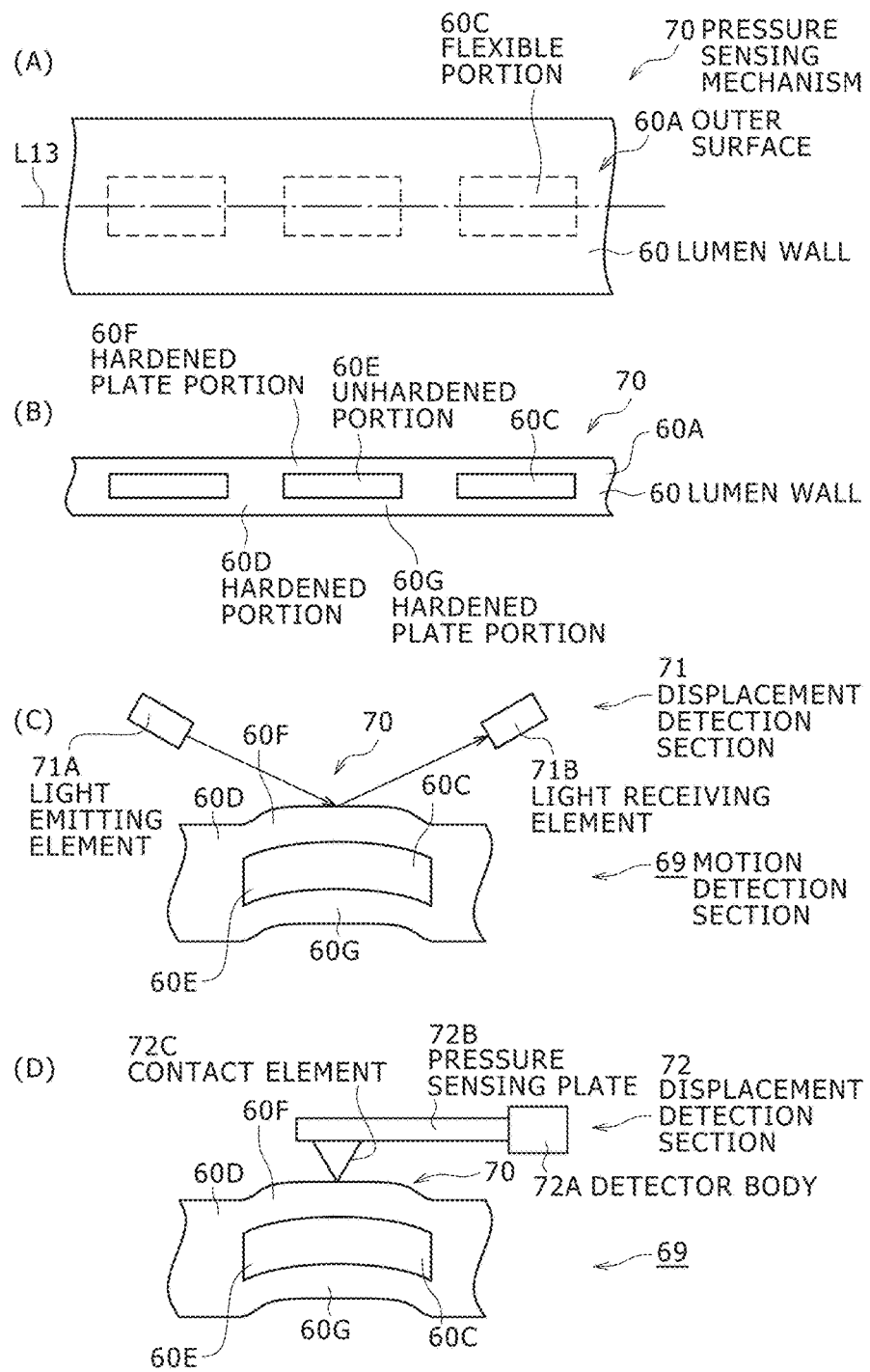
FIG. 24 is schematic views illustrating motion detection operation by a pressure sensing mechanism.
Figure 26:
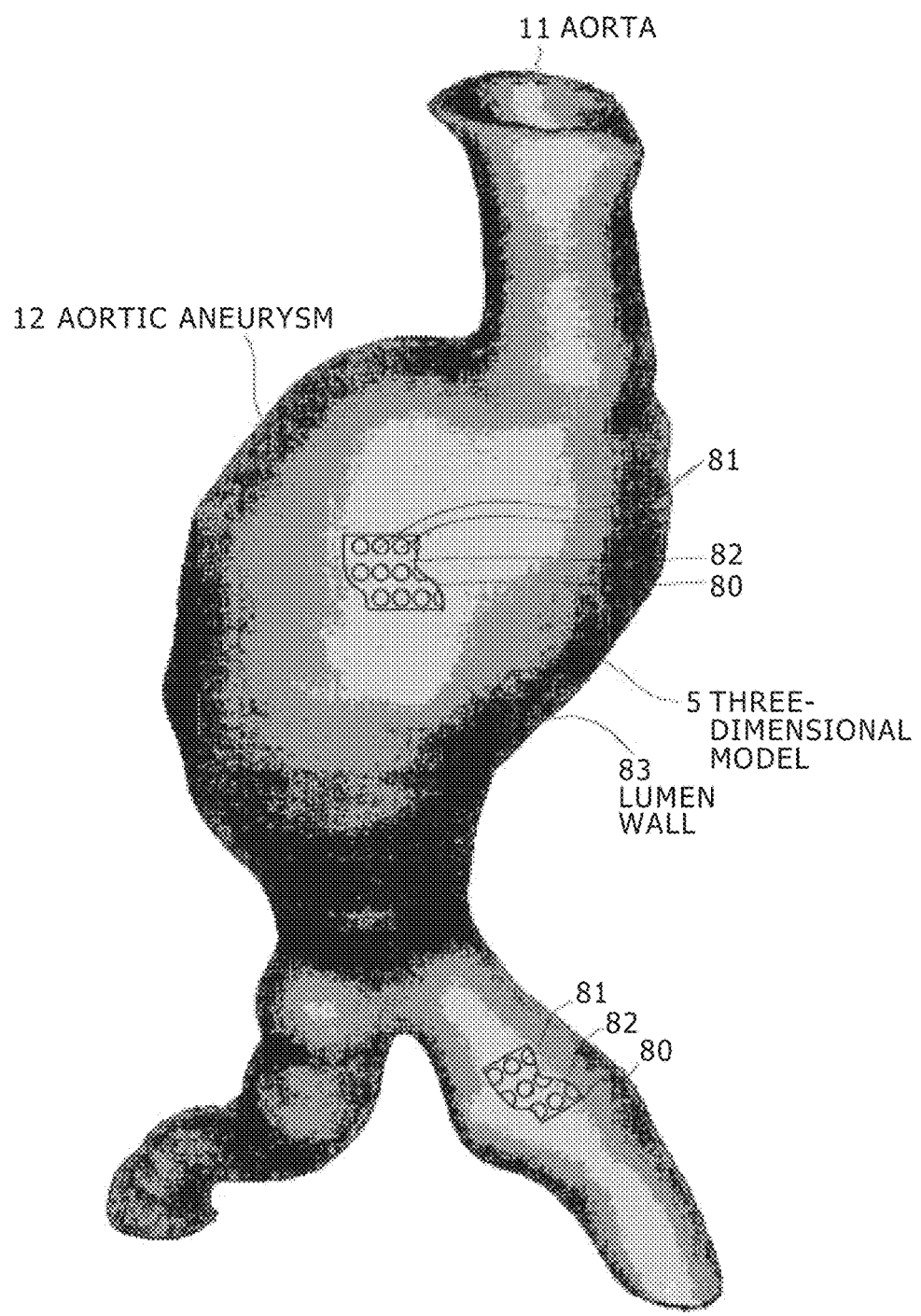
FIG. 26 is a side elevational view showing an embodiment applied to a three-dimensional model of an aorta wherein a thrombus exists in an aortic aneurysm.
Figure 27:
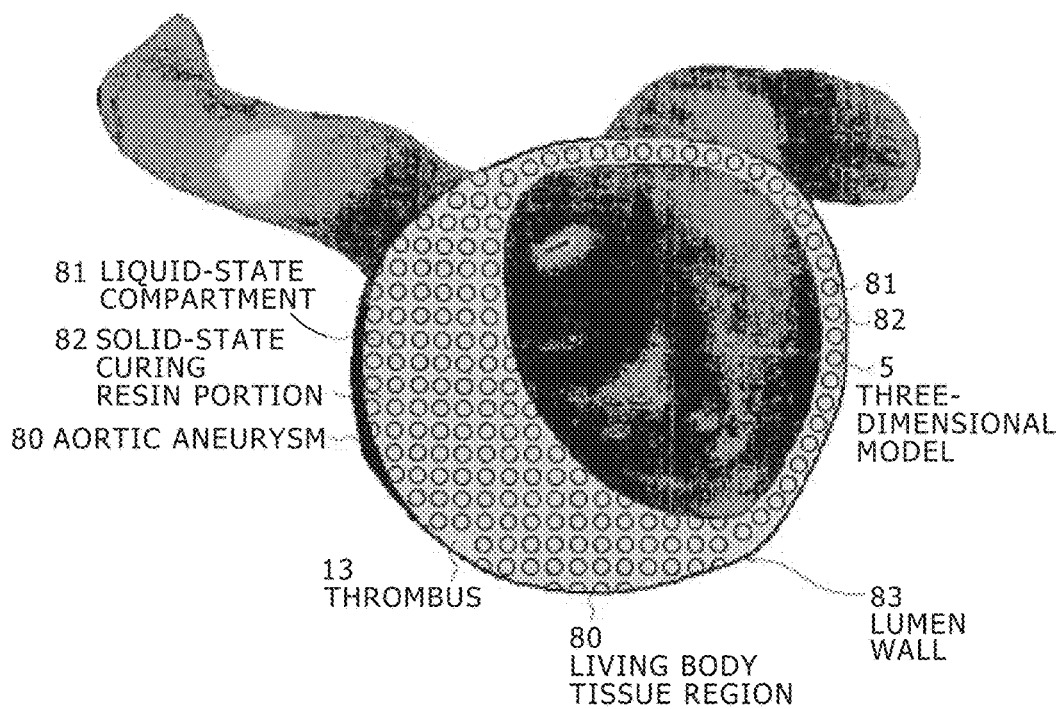
FIG. 27 is a sectional view showing a horizontal sectional structure in FIG. 26.

FIG. 24 shows a motion detection section 69 which detects a variation of the pressure in the lumen wall 60 through a pressure sensing mechanism 70 provided on the lumen wall 60. The motion detection section 69 constitutes another embodiment of means for detecting movement (displacement) of the lumen wall to allow measurement of pressure in the lumen surrounded by the lumen wall (means for measuring pressure).

In the case of the present embodiment, when a light curing process is carried out based on the tomographic shaping data S2 by the three-dimensional model production apparatus 4 (FIG. 1), the lumen wall 60 forms unhardened portions 60E in which the light curing resin remains in the form of liquid without being light-cured in a hardened portion 60D in which the light curing resin is light-cured as shown in FIG. 24(B). That is, following the energy curing, portions of the liquid-state energy-curing resin do not cure and do not harden, and those portions form the unhardened (liquid-state) portions 60E of the lumen wall 60.

In the case of the present embodiment, the hardened portion 60D has a configuration wherein a plurality of unhardened portions 60E having a rectangular shape in horizontal section and having a small thickness in vertical section are arrayed on an imaginary array line L13. By virtue of this construction, flexible portions 60C are formed in which the unhardened portions 60E are sandwiched by thin hardened plate portions 60F and 60G on the upper side and lower side positions.

Thus, while, at any other portion of the lumen wall 60 than the portions at which the unhardened portions 60E are formed, the lumen wall 60 has rigidity as an original light curing resin, at the portions at which the unhardened portions 60E are formed, the unhardened portions 60E which are intervals of the unhardened liquid-state light curing resin are supported by the thin hardened plate portions 60F and 60G. Therefore, this configuration portion forms a pressure sensing mechanism 70 which reacts with a variation of the pressure in the lumen.

This pressure sensing mechanism 70 reacts in such a manner that, if the pressure in the lumen surrounded by the lumen wall 60 becomes high, then the hardened plate portions 60F and 60G are displaced so as to move to the outer side together with the unhardened portions 60E.

In the case of the embodiment in FIG. 24(C), a displacement detection section 71 which utilizes such displacement operation of the pressure sensing mechanism 70 as just described so that detection light emitted from a light emitting element 71A is reflected by the surface of the outer side hardened plate portion 60F and received by a light receiving element 71B to detect the displacement operation of the pressure sensing mechanism 70.

Further, in the case of FIG. 24(D), a displacement detection section 72 is provided such that, when the pressure sensing mechanism 70 carries out displacement movement by the pressure in the lumen in a state in which a contact element 72C provided at an end of a pressure sensing plate 72B projecting from a detector body 72A contacts the hardened plate portion 60F on the outer side, the pressure sensing plate 72B is pushed up by the displacement movement thereby to output a detection output corresponding to the pushup amount from the detector body 72A.

With the configuration of FIG. 24, since the pressure sensing mechanism 70 which carries out displacement operation to the outer side in response to the pressure in the lumen surrounded by the lumen wall 60 is configured by providing the unhardened portions 60E which are liquid-state intervals in which the resin is not light-hardened in the lumen wall 60, the motion detection section 69 by which it is possible to obtain the shift amount of the pressure sensing mechanism 70, and accordingly a displacement detection output corresponding to the pressure in the lumen, can be effected.

Further, since, also where the lumen wall 60 having high rigidity is configured as the three-dimensional model 5, a detection output corresponding to the variation of the pressure in the inside of the lumen can be obtained, effective information to investigate the movement of the lumen wall can be obtained with regard to a living body tissue including a lesion region which can be detected by reconstructing the living body tissue.

(8) Formation Process of Liquid-State Interval

When the tomographic shaping data S2 for allowing the image data processing apparatus 3 to reconstruct a living body tissue is supplied to the three-dimensional model production apparatus 4 in the manner described above, the three-dimensional model production apparatus 4 carries out a process to form, while liquid-state compartments 81 are left in the inside of a living body tissue region 80 which does not make a bore from within a living body tissue to be targeted, solid-state curing resin 82 in the other region.

In the case of the present embodiment, a configuration is adopted such that the liquid-state compartments 81 in the form of a disk are arrayed on an imaginary array line L14 of the living body tissue region 80 and, in the liquid-state compartments 81, the liquid resin material is left without carrying out a hardening process of the liquid-state active energy curing resin thereby to enclose the liquid-state compartments 81 in the solid-state curing resin 82.

Thus, as described hereinabove with reference to FIGS. 10 and 11, such a three-dimensional model 5 that a thrombus 13 exists in an aortic aneurysm 12 as a lesion region of an aorta 11 is formed as a three-dimensional model 5 configured such that, as the portions of the lumen wall 83 (11B1 to 11B4 of FIG. 10) or the thrombus 13, the liquid-state compartments 81 are enclosed in the solid-state curing resin 82.

If a horizontal sectional face of the three-dimensional model 5 is shown, then regarding not only the lumen wall 83 but also the thrombus 13 appearing on the inner side of the aortic aneurysm 12, a soft living body tissue is produced by the configuration wherein the liquid-state compartments 81 are enclosed in the solid-state curing resin 82 which forms the lumen wall 83.

With the configuration described above, when the three-dimensional model 5 in which a living body tissue is reconstructed by the three-dimensional model production apparatus 4 based on the tomographic shaping data S2 produced by the image data processing apparatus 3, the liquid-state compartments 81 in which the resin remains in the form of liquid without being light-cured are enclosed in the solid-state curing resin 82 in a light-cured state. Therefore, the outer surface of the lumen wall 83 of the three-dimensional model 5 presents a soft touch as the liquid-state compartments 81 are enclosed.

Accordingly, when the user touches the three-dimensional model 5, since the three-dimensional model 5 has flexibility proximate to that of a living body tissue inside the body, even if the three-dimensional model 5 is used as an operation technique simulator of compatibility confirmation with a stent graft or a stent and so forth, detailed survey of the three-dimensional model 5 can be carried out without causing the user to feel an uncomfortable feeling.

Set forth below is a listing and associated description of reference numerals illustrated in the drawing figures.

1 . . . Living Body Tissue Three-Dimensional Model Production System
2 . . . Three-Dimensional Data Acquisition Apparatus
3 . . . Image Data Processing Apparatus
4 . . . Three-Dimensional Model Production Apparatus
5 . . . Three-Dimensional Model
11 . . . Aorta
11A-11A4 . . . Outer Surface
11B1-11B4 . . . Lumen Wall
11C1-11C4 . . . Blood flow Portion
11D2-11D3 . . . Thrombus Portion
12 . . . Aortic Aneurysm
13 . . . Thrombus
21 . . . Aorta
21A1-21A5 . . . Boundary
21B2-21B5 . . . Double Blood Vessel Wall
21C1-21C5 . . . Lumen Wall
22 . . . Swelling
23 . . . Double Blood Vessel Wall
31 . . . Aortic Arch of Pectoral Region
31A1-31A6 . . . Boundary
31B1-31B6 . . . Blood Flow
31C1-31C6 . . . Lumen Wall 32 . . . Brachiocephalic Artery
33 . . . Left Common Carotid Artery
34 . . . Left Subclavian Artery
41 . . . Heart
42 . . . Aorta
44 . . . Bypass Blood Vessel
45A-45D . . . Boundary
46A-46C . . . Blood Flow
47, 48 . . . Connecting Blood Vessel Portion
49 . . . Bypass Blood Vessel Portion
50B-50D . . . Blood Flow
51 . . . Flow Indicating Element
51A . . . Leg Portion\
51B . . . Flow Abutting Portion
52 . . . Lumen Wall
53 . . . Lumen Inner Face
54 . . . Lumen
60 . . . Lumen Wall
60A . . . Outer Surface
60B . . . Distortion Detecting Hole
60C . . . Flexible Portion
60D . . . Hardened Portion
60E . . . Unhardened Portion
60F, 60G . . . Hardened Plate Portion
61 . . . Motion Detecting Protrusion
62, 66, 69 . . . Motion Detection Section
70 . . . Pressure Sensing Mechanism
71 . . . Displacement Detection Section
71A . . . Light Emitting Element
71B . . . Light Receiving Element
72 . . . Displacement Detection Section
72A . . . Detector Body
72B . . . Pressure Sensing Plate
72C . . . Contact Element
80 . . . Living Body Tissue Region
81 . . . Liquid-State Compartment
82 . . . Solid-State Curing Resin Portion
83 . . . Lumen Wall The three-dimensional model and associated method disclosed here can be utilized to reconstruct a living body tissue inside the body having a lesion region.

The detailed description above describes embodiments of the three-dimensional model and associated method for producing such three-dimensional model. The invention is not limited, however, to the precise embodiment and variations described and illustrated above. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A method for producing a living body tissue three-dimensional model comprising:
    lamination shaping the living body tissue three-dimensional model using the lesion region tomographic data produced based on three-dimensional data of a lesion region of a living body tissue in which a thickness of a lumen wall portion of a lumen portion including the lesion region is reconstructed; and
    implanting a plurality of cantilever flow indicating elements into a wall of the living body tissue three-dimensional model;
    wherein the cantilever flow indicating elements are small pieces each in the form of a thin plate formed in a projecting manner from the wall and each comprising a flexible leg portion and a flow abutting portion, the flexible leg portion having one end implanted into the wall, the flow abutting portion being formed at an other end of the flexible leg portion, a width of the flow abutting portion being greater than a width of the flexible leg portion.

2. The method according to claim 1, further comprising coupling three-dimensional data with the lesion region tomographic data to form a penetrating portion of an operation instrument into a lesion region which has been reconstructed on a side face or an end face of the lumen portion.

3. The method according to claim 1, further comprising coupling three-dimensional data of an overlapping coupling portion with the lesion region tomographic data so that no offset is provided on a lumen inside face region in a state in which a coupling portion of the lumen for coupling the adjacent parts to each other is coupled.

4. The method according to claim 1, further comprising shaping the three-dimensional model using active energy-curing resin based on the tomographic image data of the living body.

5. A method for producing a living body tissue three-dimensional model comprising:
    hardening, using tomographic image data of a living body, at least a portion of an active liquid-state energy-curing resin to shape and form a three-dimensional model of the living body tissue based on the tomographic image data of the living body; and
    implanting a plurality of cantilever flow indicating elements into a wall of the three-dimensional model of the living body;
    the hardening of the at least a portion of the active liquid-state energy-curing resin being performed so that the three-dimensional model of the living body tissue comprises a liquid-state compartment in which a portion of the active liquid-state energy-curing resin remains unhardened and is surrounded by the hardened resin;
    wherein the cantilever flow indicating elements are small pieces each in the form of a thin plate formed in a projecting manner from the wall and each comprising a flexible leg portion and a flow abutting portion, the flexible leg portion having one end implanted into the wall, the flow abutting portion being formed at an other end of the flexible leg portion, a width of the flow abutting portion being greater than a width of the flexible leg portion.

6. The method according to claim 5, further comprising coupling three-dimensional data with the tomographic image data to form a penetrating portion of an operation instrument into a region which has been reconstructed on a side face or an end face of a lumen portion.

7. The method according to claim 5, further comprising coupling three-dimensional data of an overlapping coupling portion with the tomographic image data so that no offset is provided on a lumen inside face region in a state in which a coupling portion of a lumen for coupling the adjacent parts to each other is coupled.

* * * * *